(12) United States Patent
Kuwabara et al.

(10) Patent No.: US 7,632,950 B2
(45) Date of Patent: Dec. 15, 2009

(54) PYRIDYLTETRAHYDROPYRIDINES AND PYRIDYLPIPERIDINES AND METHOD OF MANUFACTURING THEM

(75) Inventors: Hirokazu Kuwabara, Tokyo (JP); Takayuki Sonoda, Kanagawa (JP); Hiromitsu Saitoh, Kanagawa (JP); Hidehiro Arai, Kanagawa (JP)

(73) Assignee: Fujifilm Finechemicals Co., Ltd, Tokyo (JP)

( * ) Notice: Subject to any disclaimer, the term of this patent is extended or adjusted under 35 U.S.C. 154(b) by 364 days.

(21) Appl. No.: 10/568,577

(22) PCT Filed: Aug. 18, 2004

(86) PCT No.: PCT/JP2004/012140

§ 371 (c)(1), (2), (4) Date: Aug. 29, 2006

(87) PCT Pub. No.: WO2005/016910

PCT Pub. Date: Feb. 24, 2005

(65) Prior Publication Data

US 2007/0093528 A1     Apr. 26, 2007

(30) Foreign Application Priority Data

Aug. 18, 2003   (JP) .............................. 2003-294287

(51) Int. Cl.
*C07D 401/04* (2006.01)

(52) U.S. Cl. ...................... 546/255; 546/256; 546/258

(58) Field of Classification Search ....................... None
See application file for complete search history.

(56) References Cited

FOREIGN PATENT DOCUMENTS

| JP | 2002-518327 A | 6/2002 |
| JP | 2002-518386 A | 6/2002 |
| WO | WO 99/65896 | * 12/1999 |
| WO | WO 01/62742 A1 | 8/2001 |
| WO | WO 03/099266 A2 | 12/2003 |

OTHER PUBLICATIONS

Vincenzo Carelli, et al., "Alcuni derivari γ-piridin-e γ-chinolin-piperidinici", Annali di Chimica, 1959, pp. 709-719, vol. 49.
Floris P.J.T. Ruties, et al., "Selective Azetidine and Tetrahydropyridine Formation via Pd-Catalyzed Cyclizations of Allene-Substituted Amines and Amino Acids", Organic Letters, 1999, pp. 717-720, vol. 1, No. 5.
International Search Report dated Dec. 7, 2004.

* cited by examiner

*Primary Examiner*—Zinna N Davis
(74) *Attorney, Agent, or Firm*—Sughrue Mion, PLLC

(57) ABSTRACT

The present invention provides pyridine derivatives useful as intermediates of drugs and agricultural chemicals, electrophotographic receptors, dyes and so on. More specifically, the invention relates to novel pyridyltetrahydropyridines and novel pyridylpiperidines, and further to a method of manufacturing pyridine derivatives through reaction between bipyridine derivatives and benzyl halide or benzyloxycarbonyl halide and subsequent reduction of the resultant reaction products with the aid of palladium catalysts, platinum catalysts, ruthenium catalysts or rhodium catalysts.

2 Claims, No Drawings

PYRIDYLTETRAHYDROPYRIDINES AND PYRIDYLPIPERIDINES AND METHOD OF MANUFACTURING THEM

This application is a 371 of PCT/JP04/12140 filed Aug. 18, 2004.

FIELD OF THE INVENTION

The present invention relates to pyridyltetrahydropyridine derivatives and pyridylpiperidine derivatives which form important intermediates in the fields of drugs, agricultural chemicals, catalyst ligands, combinatorial chemistry, organic electroluminescent devices, charge transferors, electrophotographic photoreceptors, dyes and so on, and to a method of manufacturing those derivatives.

BACKGROUND ART

Pyridyltetrahydropyridine derivatives and pyridylpiperidine derivatives are useful in the fields of drugs, agricultural chemicals, catalyst ligands, combinatorial chemistry, organic electroluminescent devices, charge transferors, electrophotographic photoreceptors, dyes and so on, and various types of those derivatives are developed already in the medicinal field in particular. For instance, the pyridyltetrahydropyridine derivatives hitherto disclosed are $\alpha_{1A}$ receptor antagonists (See Patent Document 1 and Patent Document 2; the cited documents are shown hereinafter), 5-HT$_{1A}$ receptor antagonists (See Patent Document 3), tetrabenazine antagonists (See Non-patent Document 1), TNP inhibition activators (See Patent Document 4), neurodegenerative disease fighting drugs (See Patent Document 5), and so on. And the pyridylpiperidine derivatives hitherto disclosed are, e.g., neuropeptide Y or Y5 antagonists (See Patent Document 6 and Patent Document 7), corticotropin-releasing factor inhibitors (See Patent document 8), $\alpha_{1A}$ adrenoreceptor antagonists (See Patent Document 9) and metalloprotease inhibitors (See Patent Document 10 and Patent Document 11).

On the other hand, methods of reducing bipyridines directly to pyridyltetrahydropyridine derivatives or pyridylpiperidine derivatives have not been developed yet, but these derivatives required multiple-step syntheses.

The synthesis method according to dehydration reaction of piperidinol (See Patent Document 12) is disclosed as one example of manufacturing methods of tetrahydropyridine derivatives. However, such a method has a problem in industrial-scale production since a piperidinol analogue used as the starting material is generally hard to get.

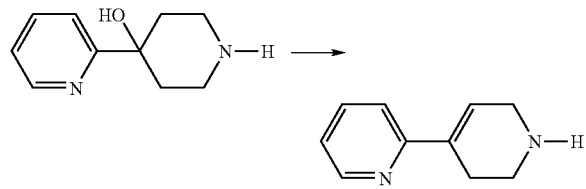

As another method, it is known that tetrahydropyridine derivatives can be synthesized by nucleophilic substitution using halogenated pyridines (See Patent Document 13). However, this synthesis requires the use of a highly toxic material, such as tributyl stannane, or a highly reactive raw material such as an organolithium compound or a Grignard compound, so it also has a problem in industrial-scale production.

Further, there is known the method of manufacturing pyridylpiperidines directly from bipyridines with the aid of nickel-aluminum alloy (See Non-patent Document 2). However, such a method requires a long reaction time of 385 hours, so a problem lies in the industrialization thereof.

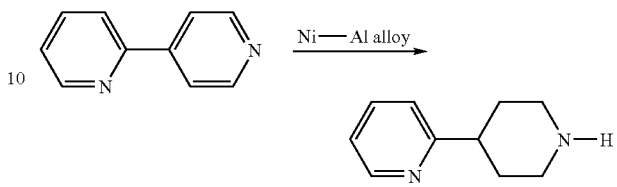

Additionally, there are known some methods for production of pyridylpiperidines from bipyridines through selective reduction of one aromatic ring alone in each bipyridine. In an example of such methods, bipyridine derivatives are oxidized by use of peroxybenzoic acid to be guided to N-oxides, and then undergo hydrogenation reaction using 10% palladium carbon as a reduction catalyst. However, such a production method requires a peroxide compound like peroxybenzoic acid, so it is difficult to enlarge the reaction scale (See Non-patent Document 3).

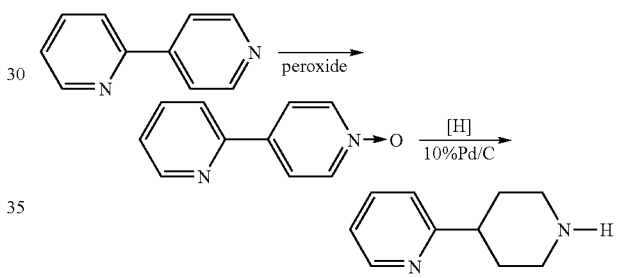

Patent Document 1: WO 99/07695
Patent Document 2: U.S. Pat. No. 6,159,990
Patent Document 3: WO 99/03847
Patent Document 4: WO 01/29026
Patent Document 5: WO 02/42305
Patent Document 6: WO 01/85714
Patent Document 7: WO 99/48888
Patent Document 8: U.S. Pat. No. 6,107,301
Patent Document 9: U.S. Pat. No. 6,316,437
Patent Document 10: WO 01/62742
Patent Document 11: WO 02/74767
Patent Document 12: JP-T-2003-512370
Patent Document 13: JP-T-11-506118
Non-patent Document 1: Walfred S. Saari, The Journal of Medicinal Chemistry, (America), The American Chemical Society, 1984, pp. 1182-1185
Non-patent Document 2: George Lunn, The Journal of Organic Chemistry, (America), The American Chemical Society, 1992, pp. 6317-6320
Non-patent Document 3: Jean-Christophe Plaquevent & Ilhame Chichaoui, Bulletin de la Societe Chimique de France, (France), Societe Chimique de France, 1996, pp. 369-380

DISCLOSURE OF THE INVENTION

Objects of the invention are to provide pyridyltetrahydropyridine derivatives and pyridylpiperidine derivatives useful in the fields of drugs, agricultural chemicals, catalyst ligands, combinatorial chemistry, organic electroluminescent devices, charge transferors, electrophotographic photoreceptors, dyes and so on, and to provide a method of manufacturing such derivatives.

As a result of our intensive studies to attain the objects, we have succeeded in developing pyridyltetrahydropyridine derivatives and pyridylpiperidine derivatives useful as intermediates for drugs, agricultural chemicals, catalyst ligands, combinatorial chemistry, electrophotographic photoreceptors, dyes and the like, and a manufacturing method thereof, thereby completing the invention.

In other words:

(1) A compound represented by the following formula (I) and a salt thereof.

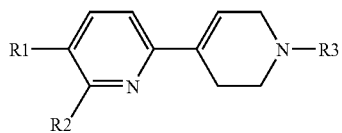

In formula (I),

R1 represents an alkyl group, an alkenyl group, an alkynyl group, an aryl group, an alkoxy group, an aryloxy group, a formyl group, a carboxyl group, a carbonyl group, an oxycarbonyl group, a sulfonyl group, a carbamoyl group, a sulfamoyl group, a thiol group, an alkylthio group, an arylthio group, a thiocarbonyl group, a ureido group, an amino group, a carbonylamino group, a sulfonylamino group, a cyano group, a heterocycle residue, a fluorine atom, a bromine atom or an iodine atom.

R2 represents a hydrogen atom or an alkyl group.

Alternatively, R1 and R2 may combine and form a ring structure.

R3 represents a hydrogen atom, an alkyl group, a formyl group, a carboxyl group, a carbonyl group, an oxycarbonyl group, a sulfonyl group, a carbamoyl group or a sulfamoyl group.

(2) A compound represented by the following formula (II) and a salt thereof.

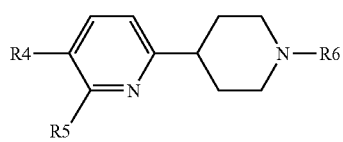

In formula (II),

R4 represents an alkyl group, an alkenyl group, an alkynyl group, an aryl group, an alkoxy group, an aryloxy group, a formyl group, a carboxyl group, a carbonyl group, an oxycarbonyl group, a sulfonyl group, a carbamoyl group, a sulfamoyl group, a thiol group, an alkylthio group, an arylthio group, a thiocarbonyl group, a ureido group, an amino group, a carbonylamino group, a sulfonylamino group, a cyano group, a heterocycle residue, a fluorine atom, a bromine atom or an iodine atom.

R5 represents a hydrogen atom or an alkyl group.

Alternatively, R4 and R5 may combine and form a ring structure.

R6 represents a hydrogen atom, an alkyl group, a formyl group, a carboxyl group, a carbonyl group, an oxycarbonyl group, a sulfonyl group, a carbamoyl group or a sulfamoyl group. Provided that R6 does not represent a methyl group when R4 and R5 combine and form a benzene ring.

(3) A compound represented by the following formula (III) and a salt thereof.

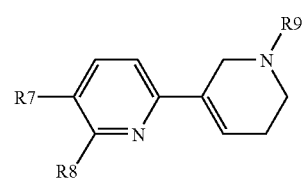

In formula (III),

R7 represents an alkyl group, an alkenyl group, an alkynyl group, an aryl group, an alkoxy group, an aryloxy group, a formyl group, a carboxyl group, a carbonyl group, an oxycarbonyl group, a sulfonyl group, a carbamoyl group, a sulfamoyl group, a thiol group, an alkylthio group, an arylthio group, a thiocarbonyl group, a ureido group, an amino group, a carbonylamino group, a sulfonylamino group, a nitro group, a cyano group, a halogen atom or a heterocycle residue.

R8 represents a hydrogen atom or an alkyl group.

Alternatively, R7 and R8 may combine and form a ring structure.

R9 represents a hydrogen atom, an alkyl group, a formyl group, a carboxyl group, a carbonyl group, an oxycarbonyl group, a sulfonyl group, a carbamoyl group or a sulfamoyl group. Provided that R9 does not represent a sulfonyl group when R7 represents a chlorine atom and R8 represents a hydrogen atom.

(4) A compound represented by the following formula (IV) and a salt thereof.

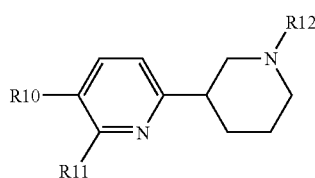

In formula (IV),

R10 represents an alkyl group, an alkenyl group, an alkynyl group, an aryl group, an alkoxy group, an aryloxy group, a formyl group, a carboxyl group, a carbonyl group, an oxycarbonyl group, a sulfonyl group, a carbamoyl group, a sulfamoyl group, a thiol group, an alkylthio group, an arylthio group, a thiocarbonyl group, an ureido group, an amino group, a carbonylamino group, a sulfonylamino group, a nitro group, a cyano group, a heterocycle residue or a halogen atom.

R11 represents a hydrogen atom or an alkyl group.

Alternatively, R10 and R11 may combine and form a ring structure.

R12 represents a hydrogen atom, an alkyl group, a formyl group, a carboxyl group, a carbonyl group, an oxycarbonyl group, a sulfonyl group, a carbamoyl group or a sulfamoyl group.

(5) A method of manufacturing a compound represented by the following formula (VI) through reaction between a bipyridine derivative represented by the following formula (V) and benzyl halide or benzyloxycarbonyl halide and subsequent reduction of the reaction product with a palladium catalyst, a platinum catalyst, a ruthenium catalyst or a rhodium catalyst.

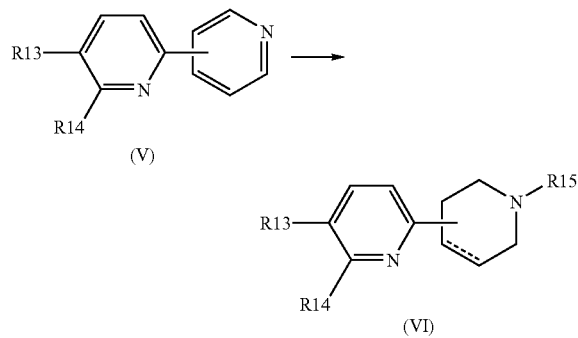

---- represents a single or double bond.

In formulae (V) and (VI),

R13 and R14 each independently represents a hydrogen atom, an alkyl group, an alkenyl group, an alkynyl group, an aryl group, an alkoxy group, an aryloxy group, a formyl group, a carbonyl group, a carboxyl group, an oxycarbonyl group, a sulfonyl group, a carbamoyl group, a sulfamoyl group, a thiol group, an alkylthio group, an arylthio group, a thiocarbonyl group, a ureido group, an amino group, a carbonylamino group, a sulfonylamino group, a nitro group, a cyano group, a halogen atom or a heterocycle residue.

Alternatively, R13 and R14 may combine and form a ring structure.

R15 represents a hydrogen atom, a benzyl group or a benzyloxycarbonyl group.

In accordance with the invention, it becomes possible to provide pyridyltetrahydropyridine derivatives and pyridylpiperizine derivatives useful as intermediates of drugs and agricultural chemicals, electrophotographic photoreceptors, dyes and the like, and further to provide a manufacturing method thereof.

BEST MODE FOR CARRYING OUT THE INVENTION

The invention is illustrated below in detail.

In the compounds represented by formulae (I) to (VI), the alkyl group represented by each of R1 to R14 specifically includes 1-20C linear, branched and cyclic alkyl groups, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclobutyl, cyclopentyl, cyclohexyl, cycloheptyl, cyclooctyl, cyclononyl and cyclodecyl etc.

The alkenyl group represented by R1, R4, R7, R10, R13 and R14 each is intended to include 2-20C linear, branched and cyclic alkenyl groups, such as vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, hexadienyl and dodecatrienyl etc.

The alkynyl group represented by R1, R4, R7, R10, R13 and R14 each is intended to include 2-20C linear, branched and cyclic alkynyl groups, such as ethynyl, butynyl, pentynyl, hexynyl, heptynyl, octynyl, nonynyl, cyclooctynyl, cyclononynyl and cyclodecynyl etc.

The aryl group represented by R1, R4, R7, R10, R13 and R14 each is intended to include 6-10C membered monocyclic or bicyclic aryl groups, such as phenyl and naphthyl etc.

The alkoxy group represented by R1, R4, R7, R10, R13 and R14 each is intended to include 1-20C alkoxy groups, such as methoxy, ethoxy, propoxy, butoxy, pentyloxy, hexyloxy, heptyloxy, octyloxy, nonyloxy, decyloxy, dodecyloxy and octadecyloxy etc.

The aryloxy group represented by R1, R4, R7, R10, R13 and R14 each is intended to include phenoxy and naphthoxy groups etc.

The carbonyl group represented by R1, R3, R4, R6, R7, R9, R10, R12, R13 and R14 each is intended to include acetyl, propionyl, butyryl, valeryl, isovaleryl, pivaloyl, lauroyl, myristoyl, benzoyl and naphthoyl groups etc.

The oxycarbonyl group represented by R1, R3, R4, R6, R7, R9, R10, R12, R13 and R14 each is intended to include methoxycarbonyl, ethoxycarbonyl, tert-butoxycarbonyl, n-decyloxycarbonyl, n-hexadecyloxycarbonyl, phenoxycarbonyl and naphthyloxycarbonyl groups etc.

The sulfonyl group represented by R1, R3, R4, R6, R7, R9, R10, R12, R13 and R14 each is intended to include methylsulfonyl, ethylsulfonyl, propylsulfonyl, butylsulfonyl, pentylsulfonyl, hexylsulfonyl, octylsulfonyl, dodecylsulfonyl, hexadecylsulfonyl, phenylsulfonyl and naphthylsulfonyl groups etc.

The carbamoyl group represented by R1, R3, R4, R6, R7, R9, R10, R12, R13 and R14 each is intended to include carbamoyl; monosubstituted carbamoyl groups, such as N-methylcarbamoyl, N-(tert-butyl)carbamoyl, N-dodecylcarbamoyl, N-octadecylcarbamoyl and N-phenylcarbamoyl; and disubstituted carbamoyl groups, such as N,N-dimethylcarbamoyl, N,N-dihexylcarbamoyl, N,N-didodecylcarbamoyl and N,N-diphenylcarbamoyl etc.

The sulfamoyl group represented by R1, R3, R4, R6, R7, R9, R10, R12, R13 and R14 each is intended to include sulfamoyl; monosubstituted sulfamoyl groups, such as N-ethylsulfamoyl, N-(iso-hexyl)sulfamoyl, N-ethylsulfamoyl, N-decylsulfamoyl, N-hexadecylsulfamoyl and N-phenylsulfamoyl; and disubstituted sulfamoyl groups, such as N,N-dimethylsulfamoyl, N,N-dibutoxysulfamoyl, N,N-dioctylsulfamoyl, N,N-tetradecylsulfamoyl and N,N-diphenylsulfamoyl etc.

The alkylthio group represented by R1, R4, R7, R10, R13 and R14 each is intended to include 1-20C alkylthio groups, such as methylthio, ethylthio, propylthio, butylthio, pentylthio, hexylthio, heptylthio, octylthio, nonylthio, decylthio, dodecylthio and hexadecylthio etc. The arylthio group represented by R1, R4, R7, R10, R13 and R14 each is intended to include phenylthio and naphthylthio groups etc.

The thiocarbonyl group represented by R1, R4, R7, R10, R13 and R14 each is intended to include methylthiocarbonyl, ethylthiocarbonyl, butylthiocarbonyl, octylthiocarbonyl, decylthiocarbonyl, tetradecylthiocarbonyl, octadecylthiocarbonyl, phenylthiocarbonyl and naphthylthiocarbonyl groups etc.

The ureido group represented by R1, R4, R7, R10, R13 and R14 each is intended to include ureido, N-methylureido, N-(tert-butyl)ureido, N-octylureido, N-hexadecylureido, N-phenylureido, N,N-diethylureido, N,N-dipropylureido, N,N-dihexylureido, N,N-didecylureido, N,N-dioctadecylureido and N,N-diphenylureido groups etc.

The amino group represented by R1, R4, R7, R10, R13 and R14 each is intended to include amino; monosubstituted amino groups, such as N-methylamino, N-butylamino, N-hexylamino, N-decylamino, N-tetradecylamino, N-octadecylamino, N-phenylamino and N-naphthylamino; and disubstituted aminogroups, such as N,N-diethylamino, N,N-diheptylamino, N,N-dioctylamino, N,N-dodecylamino, N,N-octadecylamino and N,N-diphenylamino etc.

The carbonylamino group represented by R1, R4, R7, R10, R13 and R14 each is intended to include acetylamino, ethylcarbonylamino, tert-butylcarbonylamino, n-octylcarbonylamino, n-hexadecylcarbonylamino, benzoylamino, naphthoylamino, methoxycarbonylamino, ethoxycarbonylamino, n-octyloxycarbonylamino and n-hexadecyloxycarbonylamino groups etc.

The halogen atom represented by R7, R10, R13 and R14 each is intended to include a chlorine atom, a bromine atom, an iodine atom and a fluorine atom etc.

The heterocycle residue represented by R1, R4, R7, R10, R13 and R14 each is intended to include residues of 5- to 10-membered monoheterocycles or biheterocycles which each contains 1 to 4 heteroatoms selected from among nitrogen, oxygen and sulfur atoms, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran and benzothiophene etc.

Those substituents relating to R1 to R14 may have additional substituents, which have no particular restrictions. Examples of the additional substituents include alkyl, alkenyl, phenyl, hydroxyl, alkoxy, phenoxy, amino, alkylthio, phenylthio, halogen atoms and heterocycle residues etc., but not necessarily limited to these ones. Further, these additional substituents may have substituents, such as alkyl, phenyl, amino or halogen atoms etc.

Alternatively, a ring structure may be formed by combining R1 with R2, R4 with R5, R7 with R8, R10 with R11 or R13 with R14. Examples of the ring formed include partially saturated rings, such as cyclopentene, cycohexene and cyclooctene etc.; aromatic rings, such as benzene and naphthalene etc.; and heterocycles, such as pyrrole, dihydropyrrole, pyridine, pyran and dihydropyran etc. These rings may further have substituents, which have no particular restrictions.

In the present compounds, R1 and R4 each is preferably a 1-12C alkyl group, a 6-10C aryl group, a substituted or unsubstituted amino group, a bromine atom or an iodine atom, more preferably an unsubstituted amino group or a bromine atom.

R2, R5, R8 and R11 each is preferably a hydrogen atom or a 1-12C alkyl group, more preferably a hydrogen atom, a methyl group or an ethyl group.

R3 is preferably a hydrogen atom, a 1-12C alkyl group or an oxycarbonyl group, more preferably a hydrogen atom, a methyl group, an ethyl group or an alkoxycarbonyl group, particularly preferably a hydrogen atom, a methyl group or an ethyl group.

R6, R9 and R12 each is preferably a hydrogen atom, a 1-12C alkyl group or an oxycarbonyl group, more preferably a hydrogen atom, a methyl group, an ethyl group or an alkoxycarbonyl group, particularly preferably a hydrogen atom, an aryl-substituted methyl group or an aryl-substituted alkoxycarbonyl group. However, R6 does not represent a methyl group when R4 and R5 combine and form a benzene ring. In addition, R9 does not represent a sulfonyl group when R7 is a chlorine atom and R8 is hydrogen atom.

R7, R10, R13 and R14 each is preferably a 1-12C alkyl group, a 6-10C aryl group, a substituted or unsubstituted amino group, a nitro group or a halogen atom, more preferably an unsubstituted amino group, a nitro group or a bromine atom.

The present compounds are converted to their salts in accordance with known methods.

Examples of such salts include alkali metal salts, alkaline earth metal salts, ammonium salts, amine salts, and acid addition salts etc. More specifically, these salts include alkali metal salts, such as sodium and potassium etc.; alkaline earth metal salts, such as calcium and magnesium etc.; ammonium salts, such as tetramethylammonium etc.; and organic amine salts, such as triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine etc.

Suitable examples of acid addition salts include inorganic acid addition salts, such as hydrochloride, hydrobromide, hydroiodide, sulfate, phosphate and nitrate; and organic acid salts, such as acetate, lactate, tartrate, benzoate, citrate, methanesulfonate, ethanesulfonate, benzenesulfonate, toluenesulfonate, isethionate, glucuronate and gluconate etc.

Next the synthesis method according to the invention is described below in detail.

The present synthesis method consists in that pyridylpyridine derivatives (hereinafter abbreviated as "bipyridines") as starting materials, which are represented by formula (V), are made to react with benzyl halides or benzyloxycarbonyl halides in the presence of appropriate solvents, and then the intermediates thus obtained are hydrogenated with at least one of catalysts such as palladium, platinum, ruthenium or rhodium, and thereby they are led to pyridyltetrahydropyridines or pyridylpiperidines represented by formula (VI) as intended products (hereinafter abbreviated as "pyridyltetrahydropyridines" or "pyridylpiperidines", respectively). As an example of such a reaction scheme, the case of using a 2,4-dipyridine derivative as the starting material and allowing the derivative to react with benzyl bromide is illustrated below. However, this case should not be construed as limiting the scope of the invention.

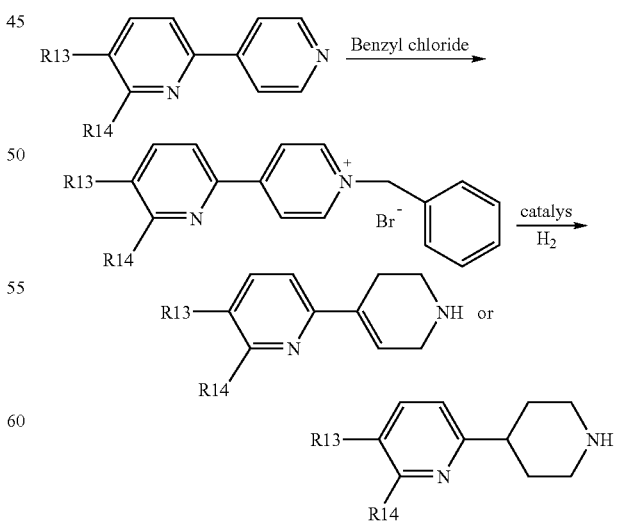

With respect to the bipyridine derivatives as starting materials, various commercial products can be utilized. Alternatively, those derivatives can be synthesized using known methods, e.g., the methods disclosed in JP-A-2000-355580, JP-A-2001-261646 and JP-A-2001-261647.

Examples of benzyl halides usable in the invention include benzyl chloride, benzylbromide and benzyl iodide. And examples of benzyloxycarbonyl halides usable in the invention include benzyloxycarbonyl chloride, benzyloxycarbonyl bromide and benzyloxycarbonyl iodide. Of these halides, benzyl chloride, benzyl bromide and benzyloxycarbonyl chloride are preferred over the others, and the more preferred one is benzyl bromide. The amount of benzyl halides used is preferably 0.5 to 2.0 times by mole, more preferably 0.9 to 1.2 times by mole, per 1 mol of a bipyridine derivative. The amount of benzyloxycarbonyl halides used is preferably 0.5 to 3.0 times by mole, more preferably 1.0 to 1.5 times by mole, per 1 mol of a bipyridine derivative.

The reactions between bipyridine derivatives and benzyl halides or benzyloxycarbonyl halides are carried out at a reaction temperature ranging from 0 to 200° C., preferably from 10 to 100° C., more preferably from 20 to 80° C. These reactions are generally completed within 24 hours. Disappearance of the starting materials is recognized within a time of 10 minutes to 12 hours in many cases, and the suitable reaction time is from 10 minutes to 4 hours.

Then, the intermediates thus obtained undergo catalytic hydrogenation in the presence of a hydrogenation catalyst.

The hydrogenation catalyst used in the invention is chosen from palladium catalysts, platinum catalysts, ruthenium catalysts or rhodium catalysts. Examples of the palladium catalysts include palladium carbon, palladium carbon poisoned by a sulfur compound, supported catalysts such as a palladium-supported silica catalyst, a palladium-supported alumina catalyst, a palladium-supported barium sulfate catalyst and a palladium-supported zeolite catalyst, palladium black, Raney palladium, metal palladium, palladium hydroxide, and palladium oxide. Examples of the platinum catalysts include platinum carbon, platinum carbon poisoned by a sulfur compound, supported catalysts such as a platinum-supported silica catalyst and a platinum-supported alumina catalyst, metal platinum, platinum black, and platinum dioxide (Adam's catalyst). Examples of the ruthenium catalysts include supported catalysts such as a ruthenium-supported silica, a ruthenium-supported alumina and a ruthenium-supported carbon, ruthenium black, ruthenium chloride and ruthenium oxide. Examples of the rhodium catalysts include supported catalysts such as a rhodium-supported silica catalyst, a rhodium-supported alumina catalyst and a rhodium-supported carbon catalyst, metal rhodium, rhodium black, rhodium chloride and rhodium oxide. Of these catalysts, palladium carbon poisoned by a sulfur compound, platinum carbon poisoned by a sulfur compound and platinum dioxide (Adam's catalyst) are used to advantage over the others. And the palladium carbon poisoned by a sulfur compound is preferable by far. The amount of a catalyst used is generally from 0.001 to 2 times by weight, preferably from 0.005 to 1 times by weight, more preferably from 0.008 to 0.08 times by weight, based on the amount of a bipyridine derivative. Further, two or more kinds of catalysts can used in a mixed condition, and the mixing ratio between them can be determined arbitrarily.

Of the catalysts recited above, in the case of synthesizing pyridyltetrahydropyridines of the present compounds, palladium carbon poisoned by a sulfur compound, platinum carbon poisoned by a sulfur compound and platinum dioxide (Adam's catalyst) are preferred over the others, and those preferable by far are palladium carbon poisoned by a sulfur compound and platinum carbon poisoned by a sulfur compound. In the case of synthesizing pyridylpiperidines, on the other hand, palladium carbon, platinum carbon and platinum dioxide (Adam's catalyst) are preferred over the others, and those preferable by far are palladium carbon and platinum dioxide (Adam's catalyst).

In the case of synthesizing pyridyltetrahydropyridines, the amount of catalysts used is generally from 0.001 to 2 times by weight, preferably from 0.005 to 1 times by weight, more preferably from 0.008 to 0.08 times by weight, based on the amount of a bipyridine derivative. In the case of synthesizing pyridylpiperidines, the amount of catalysts used is generally from 0.001 to 2 times by weight, preferably from 0.005 to 1 times by weight, more preferably from 0.008 to 0.1 times by weight, based on the amount of a bipyridine derivative. The reduction reaction is generally carried out at a reaction temperature ranging from 20 to 200° C., and the reaction temperature range is preferably from 20 to 100° C., more preferably from 30 to 80° C.

Besides being hydrogen gas, the hydrogen source which can be used herein is 3-6C secondary alcohol, such as isopropanol; cyclohexene; 1,3-cyclohexadiene; hydrazine; phosphinic acid; an alkali metal hypophosphite, such as sodium hypophosphite or potassium hypophosphite; indoline; formic acid, or a salt consisted of an ammonium such as an ammonium formate, triethylamine, alkali or alkaline earth metal or hydrogen halide. These hydrogen sources can be used as a mixture of two or more thereof, and the mixing ratio between them can be determined arbitrarily. The hydrogen pressure under which the reduction is carried out is generally within the range of 10 to 20,000 kPa, and it is preferably from 100 to 10,000 kPa, more preferably from 100 to 1,000 pKa, in the case of synthesizing pyridyltetrahydropyridines. In the case of synthesizing pyridylpiperidines, the hydrogen pressure is preferably from 100 to 10,000 kPa, more preferably from 300 to 1.000 pKa. These reactions are generally completed within 24 hours, and disappearance of starting materials is recognized within a time of 30 minutes to 12 hours in many cases.

The solvents used in those reactions may be any of solvents, irrespective of whether they are polar or non-polar, which include water; aromatic solvents, such as benzene, toluene, xylene, chlorobenzene and dichlorobenzene; polar solvents, such as pyridine, acetonitrile, N,N-dimethylformamide, N,N-dimethylacetamide and N-methylpyrrolidone; ester solvents, such as methyl acetate, ethyl acetate and butyl acetate; alcohol solvents, such as methanol, ethanol, butanol and t-butanol; and ether solvents, such as diethyl ether, diisopropyl ether, dibutyl ether, methyl t-butyl ether and tetrahydrofuran. Of these solvents, preferable ones are water and alcohol solvents, such as methanol, ethanol, isopropyl alcohol, butanol and t-butanol, and those preferred by far are methanol, ethanol and isopropyl alcohol. In addition, two or more of the solvents may be used in a mixed condition. Herein, the mixing ratio between them can be determined arbitrarily. The amount of reaction solvents used is 1 to 50 times by weight, preferably 2 to 30 times by weight, more preferably 5 to 10 times by weight, based on the amount of a bipyridine derivative.

Examples of a method for purifying pyridyltetrahydropyridines or pyridylpiperidines as the present compounds after conclusion of the reaction include extraction with water and an organic solvent, such as ethyl acetate or toluene, recrystallization with alcohol, hexane, toluene or the like, purification on a column of silica gel, alumina or the like, and reduced-pressure distillation. When the purification is performed using a single or two or more of those methods in combination, it is possible to obtain the intended products at high purities.

Examples of the present compounds are illustrated below, but the invention should not be construed as being limited to these ones.
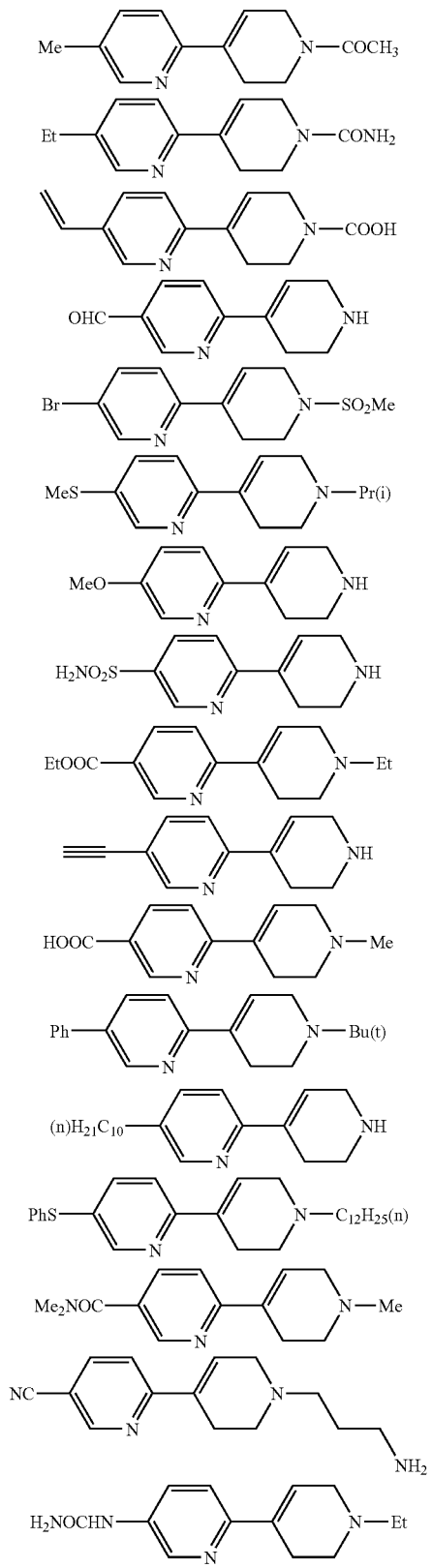
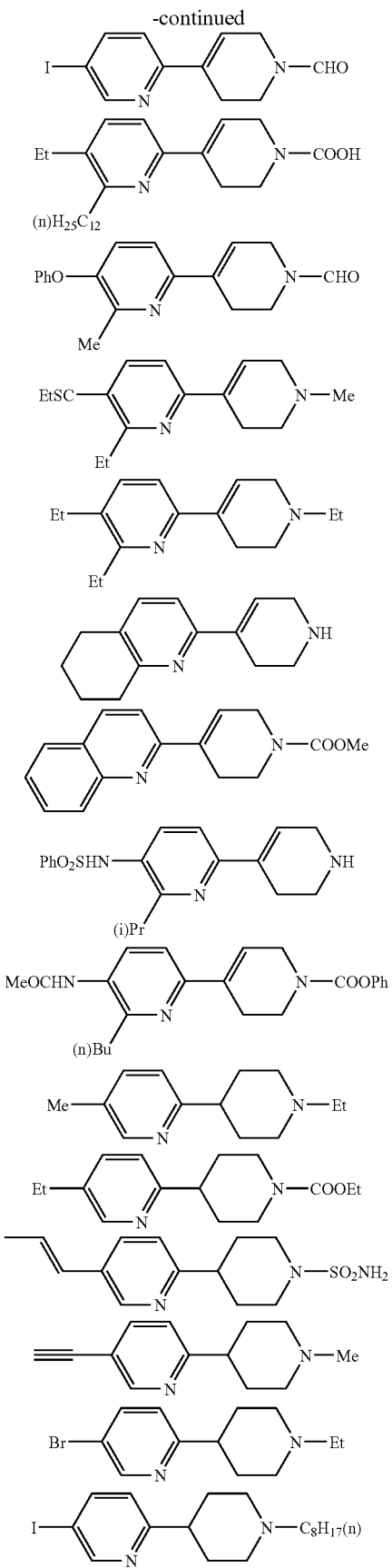

-continued
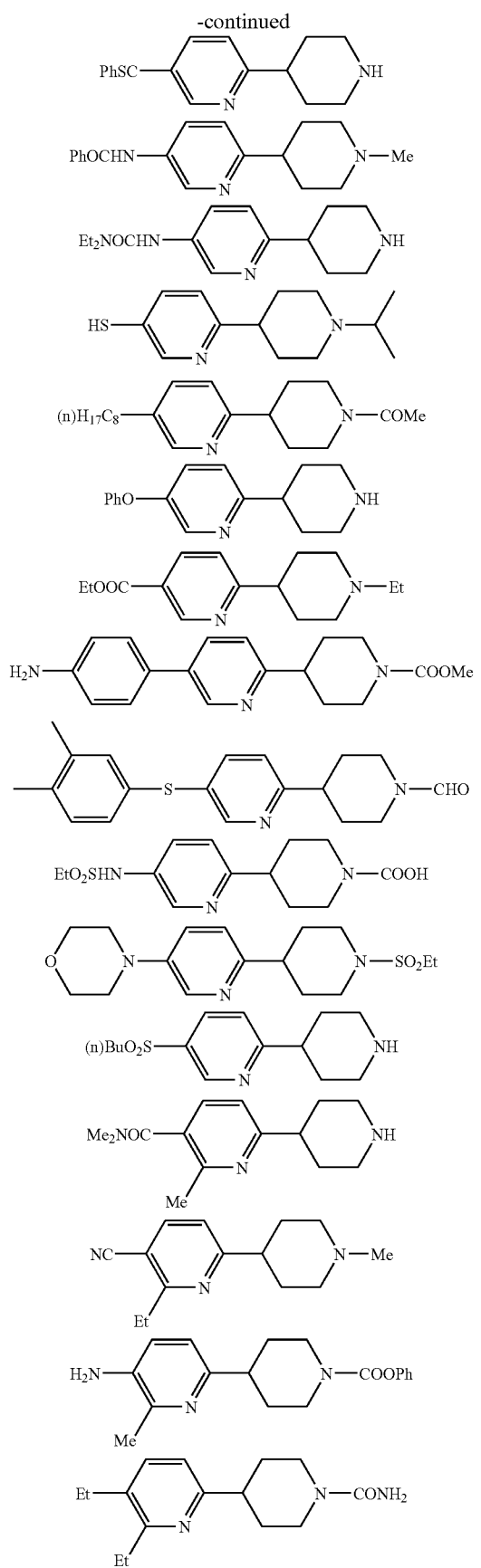
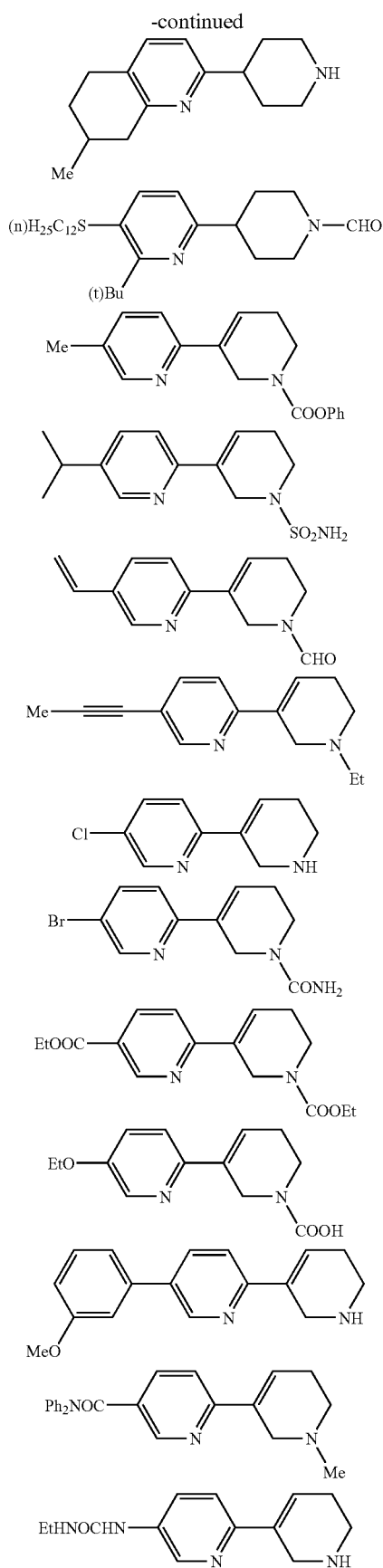

-continued
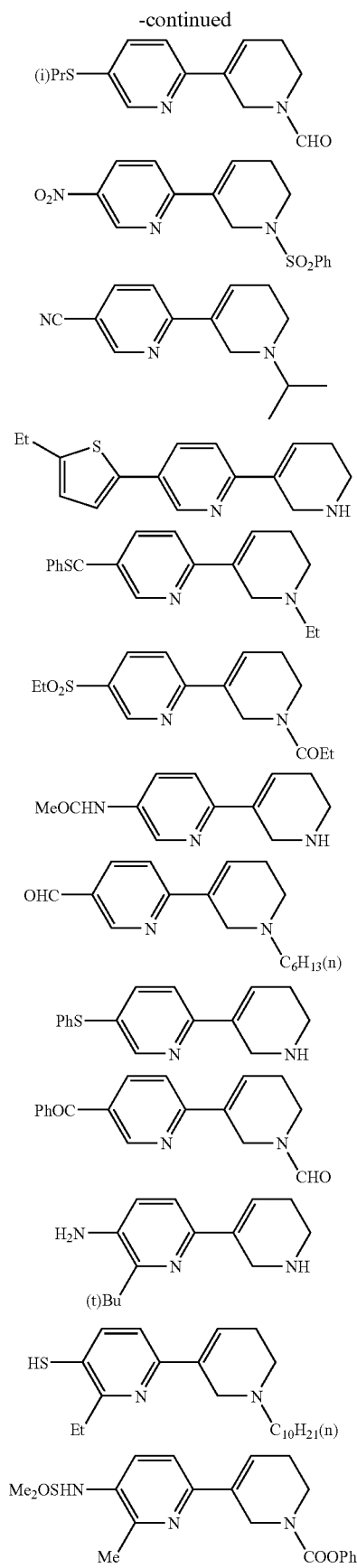
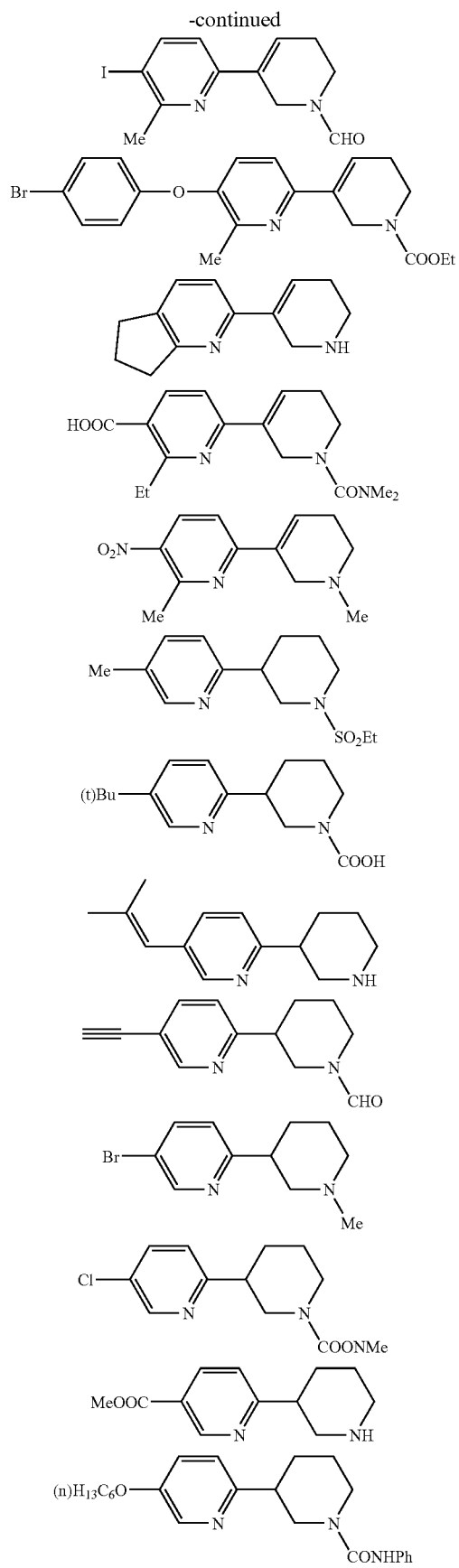

-continued
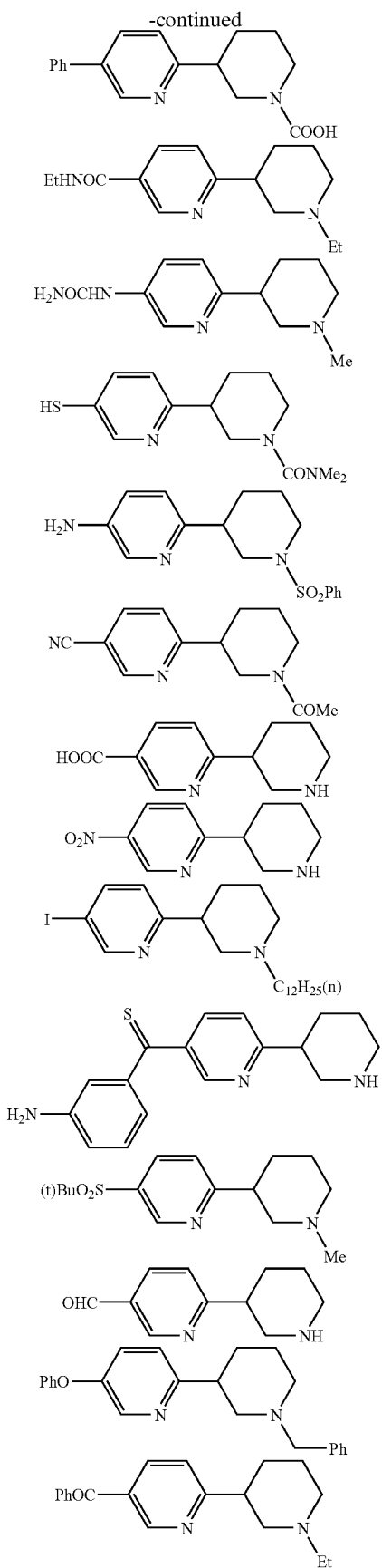
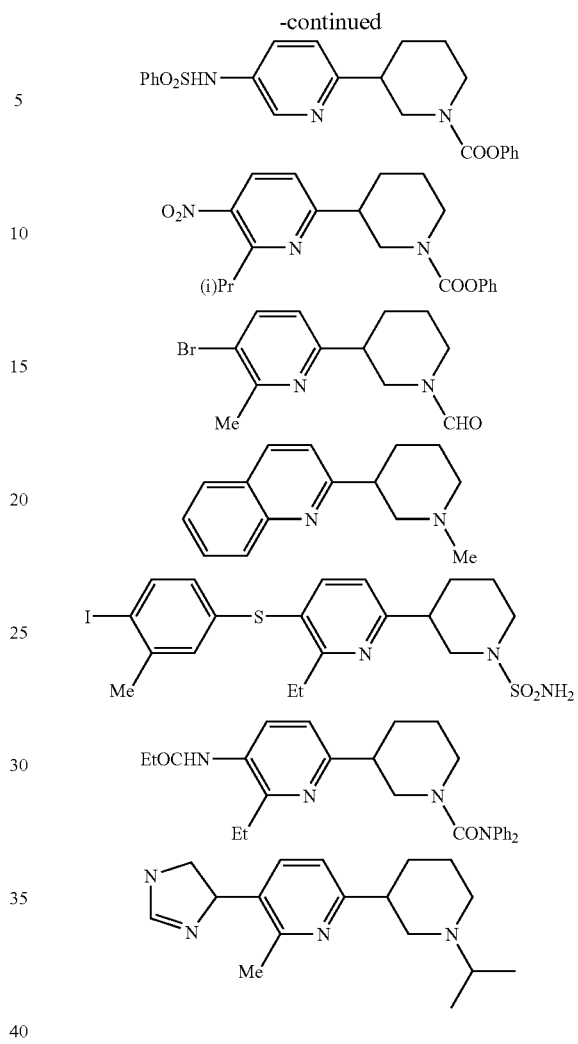
In addition, examples of compounds other than the foregoing compounds obtained in accordance with the present manufacturing method are illustrated below, and the invention is free of limitations to these compounds.
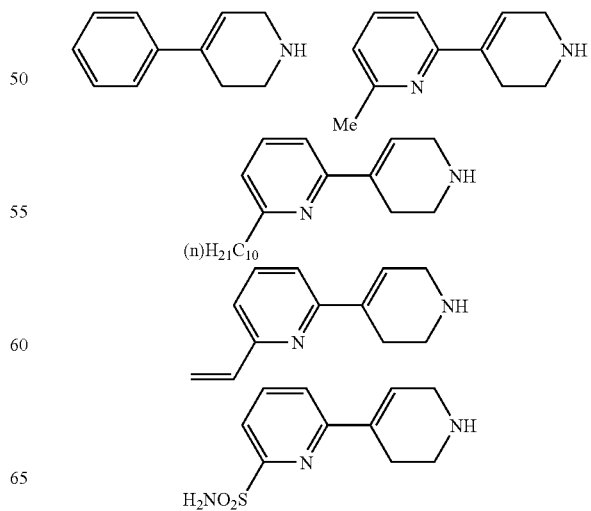

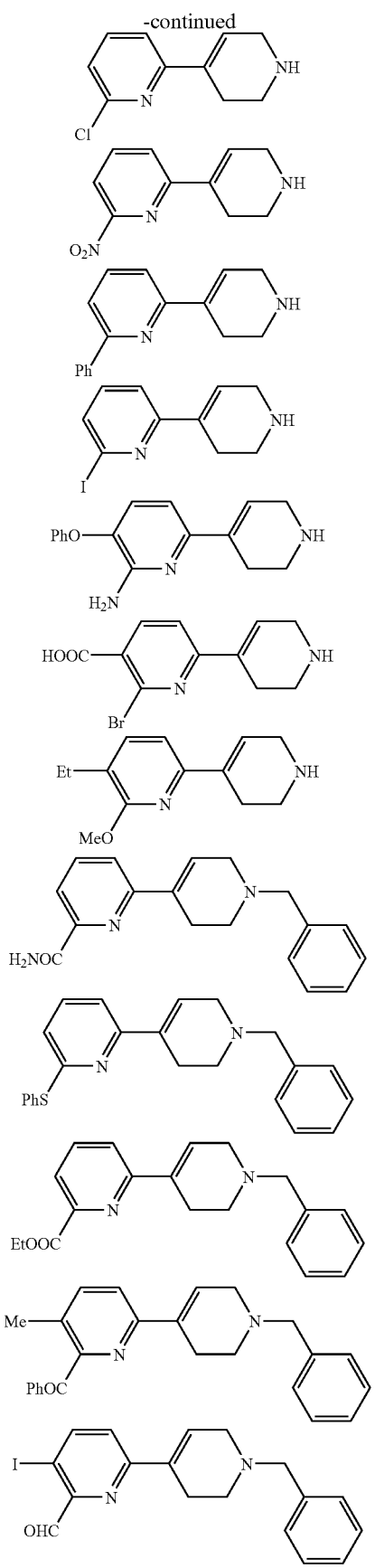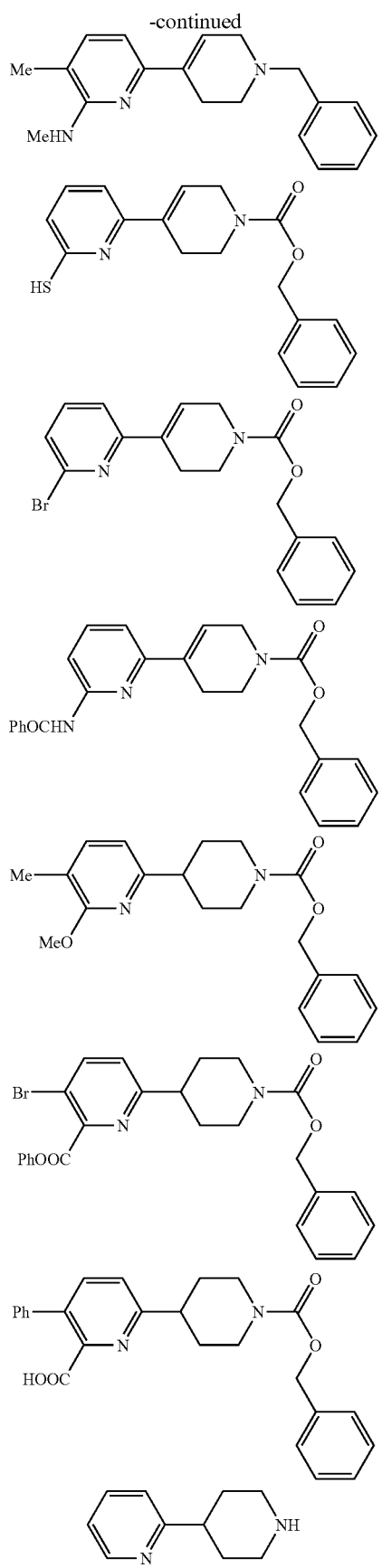

-continued
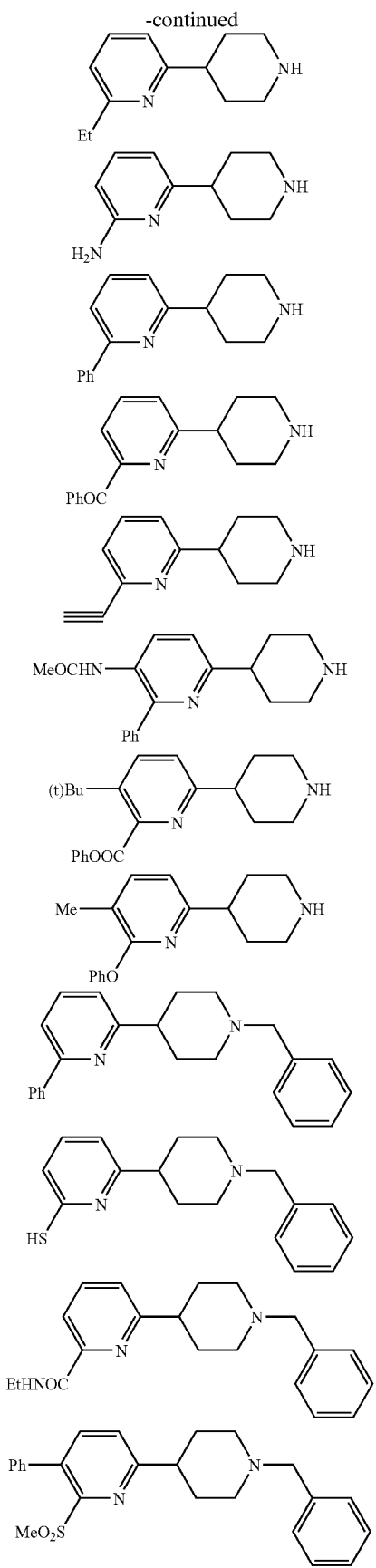
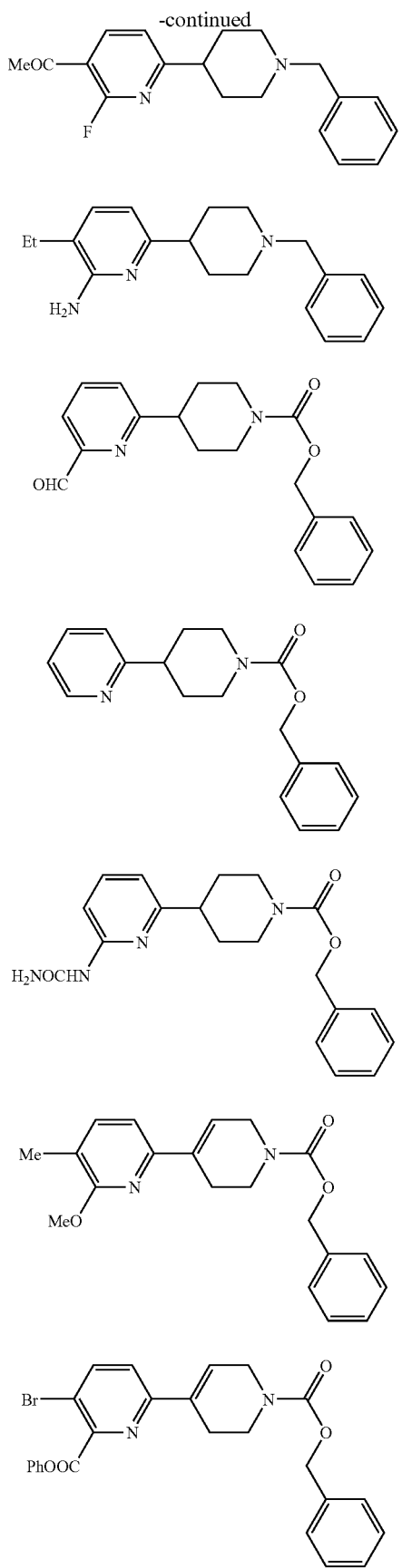

-continued
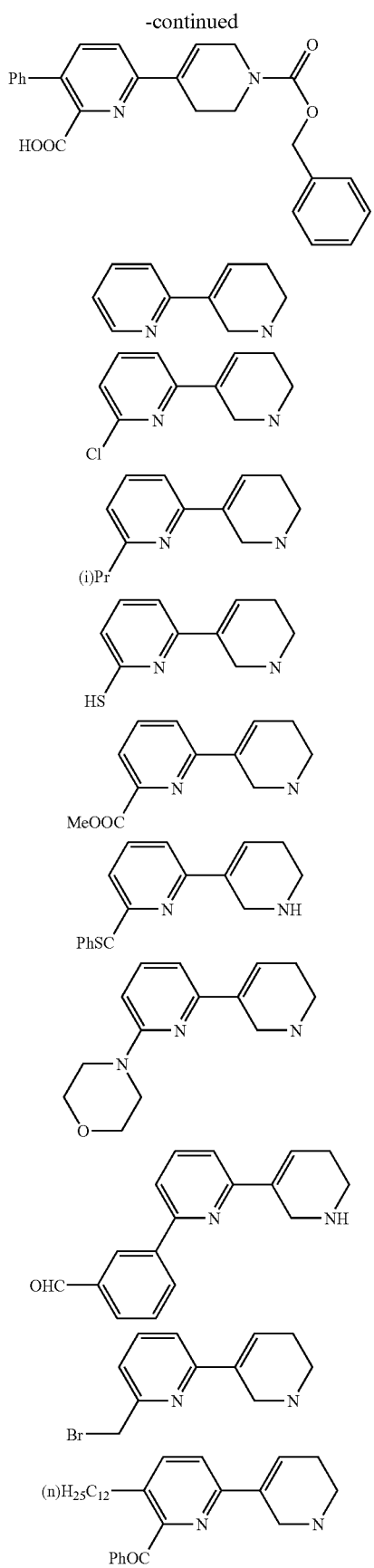
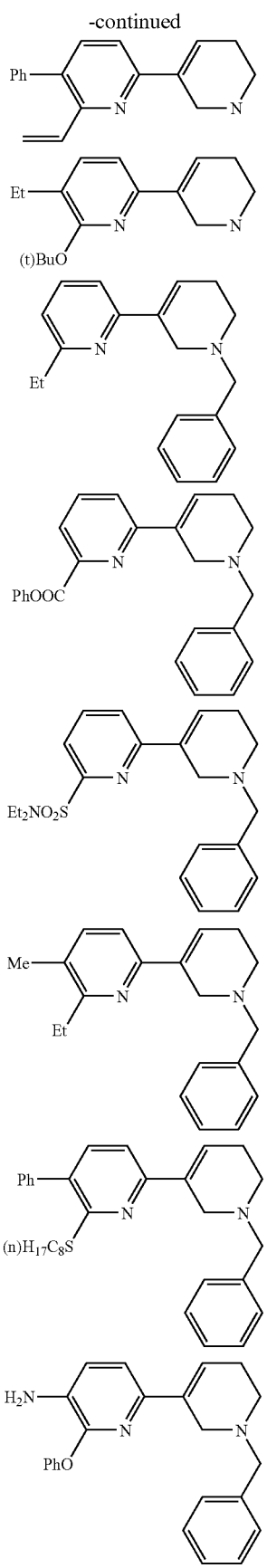

-continued
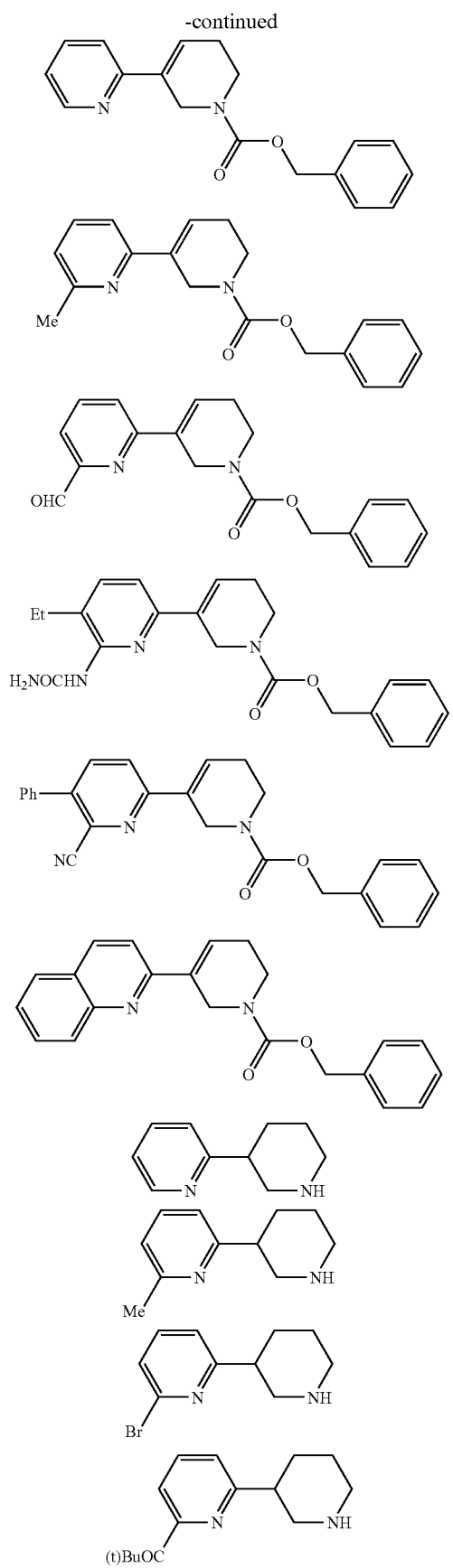
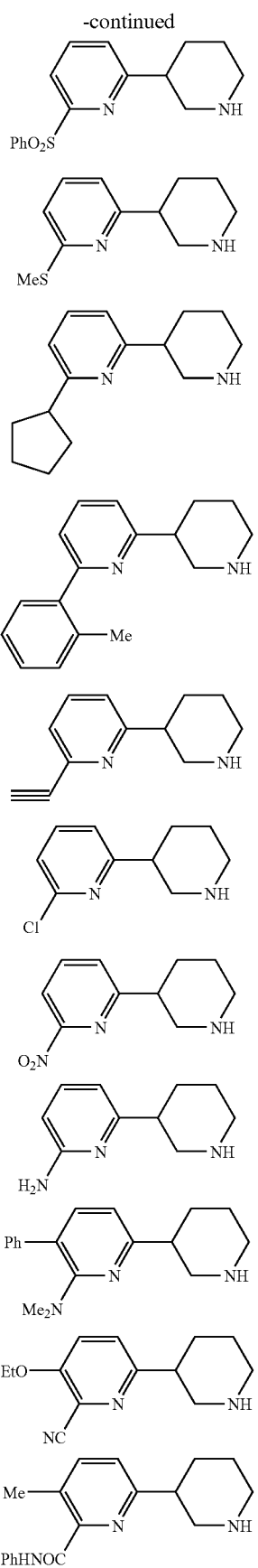

-continued

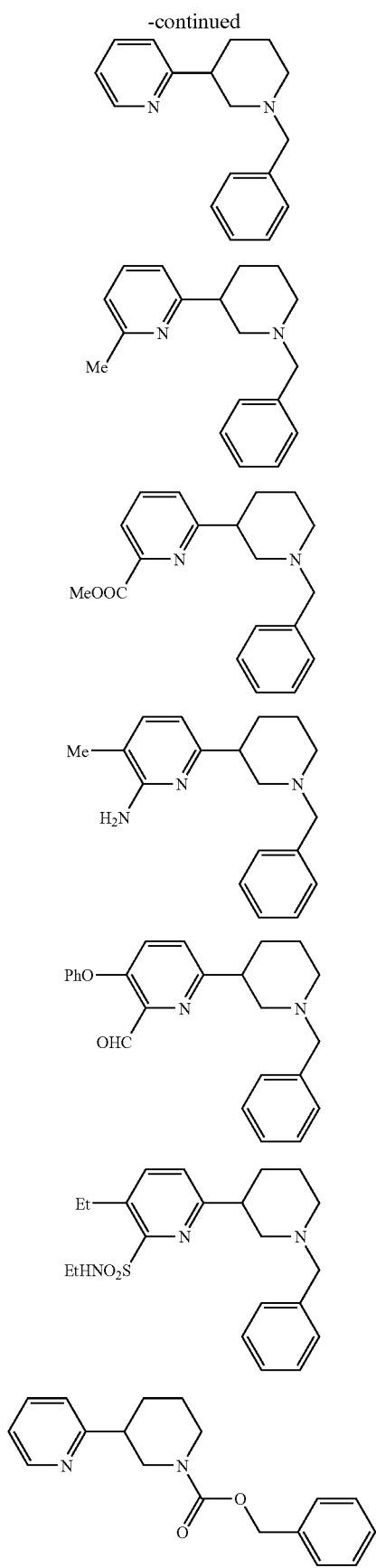

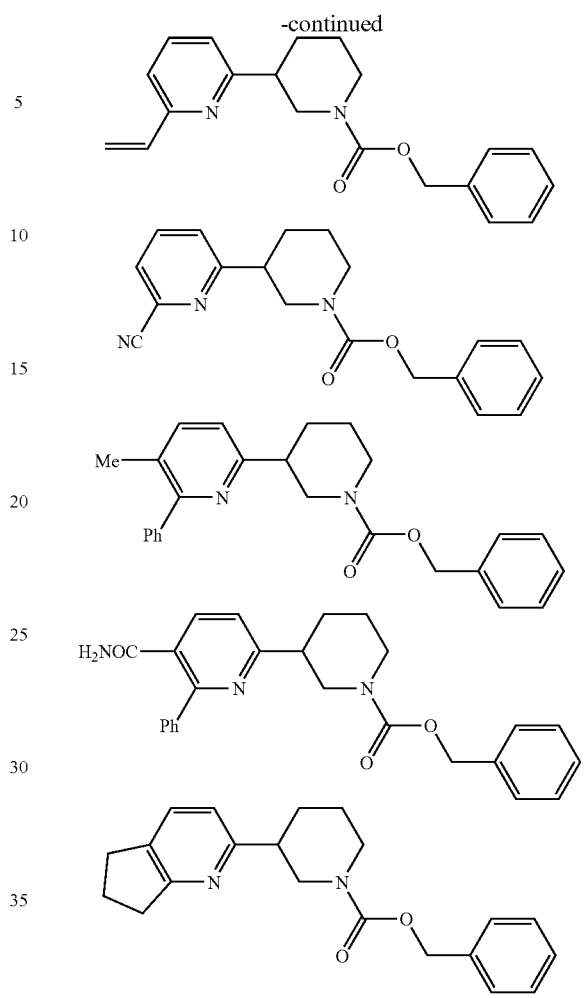

EXAMPLES

Next the invention is described in more concrete form by reference to examples, but the invention should not be construed as being limited to these examples. The structural analyses were made with the aid of $^1$H-NMR and mass spectra.

Example 1

Synthesis of 4-(5'-Methylpyrid-2'-yl)piperidine ((II)-1)

Benzyl bromide in an amount of 10.5 g was added to a solution of 10 g of 5-methyl-2,4'-bipyridine in 70 mL of isopropyl alcohol, and stirred for 5 hours at 50° C. To the resulting reaction solution, 1.69 g of 10% palladium carbon and 4.53 g of ammonium acetate were added. This admixture was put in an autoclave, the autoclave's atmosphere was replaced twice with nitrogen gas under a nitrogen pressure of 196 kPa, and then hydrogen gas was blown into the autoclave over 5 hours at 80° C. under a hydrogen pressure of 490 kPa until the absorption of hydrogen gas in a volume of 5,400 mL was completed. After the replacement with nitrogen, the catalyst was filtered out and the resulting filtrate was concentrated under a reduced pressure of 1.33 kPa until the quantity thereof was reduced to 14.0 g. Further thereto, 50 mL of water and 10 g of a 25% aqueous solution of sodium hydroxide were added. The resulting solution was extracted with three 200 mL portions of ethyl acetate, and the organic layer was concentrated. The thus deposited crystals were dried to give 5.00 g of the intended compound as light yellow crystals. Yield rate: 48%, EI-MS: (m/z) 176 (M⁺) melting point: 90.2-92.0° C.

Example 2

Synthesis of 5-Methyl-1',2',5',6'-tetrahydro-[2,4']-bipyridine ((I)-1)

Benzyl bromide in an amount of 10.5 g was added to a solution of 10 g of 5-methyl-2,4'-bipyridine in 70 mL of isopropyl alcohol, and stirred for 5 hours at 50° C. To the resulting reaction solution, 1.0 g of 2% palladium-S carbon and 6.0 g of triethylamine were added. This admixture was put in an autoclave, the autoclave's atmosphere was replaced twice with nitrogen gas under a nitrogen pressure of 196 kPa, and then hydrogen gas was blown into the autoclave over 3 hours at 80° C. under a hydrogen pressure of 196 kPa until the absorption of hydrogen gas in a volume of 4,200 mL was completed. After the replacement with nitrogen, the catalyst was filtered out and the resulting filtrate was concentrated under a reduced pressure of 1.33 kPa until the quantity thereof was reduced to 18.0 g. Further thereto, 50 mL of water and 10 g of a 25% aqueous solution of sodium hydroxide were added. The resulting solution was extracted with three 200 mL portions of ethyl acetate, and the organic layer was concentrated. The thus obtained solid was adsorbed to NH₂-modified silica gel (produced by Biotage Japan, Ltd.), and eluted with ethylacetate. The fraction obtained was concentrated, and the crystals thus deposited were dried to give 4.1 g of the intended compound as light yellow crystals. Yield rate: 40%, EI-MS: (m/z) 174 (M⁺), melting point: 78-80° C.

Example 3

Synthesis of 5,6-Dimethyl-1',2',5',6'-tetrahydro-[2,3'] bipyridine ((I)-34)

Benzyl bromide in an amount of 1.06 g was added to a solution of 1 g of 5,6-dimethyl-2,3'-bipyridine in 15 mL of isopropyl alcohol, and stirred for 5 hours at 50° C. to finish the reaction. To the reaction solution, 0.18 g of 10% palladium carbon and 0.59 g of triethylamine were added. This admixture was put in an autoclave, the autoclave's atmosphere was replaced twice with nitrogen gas under a nitrogen pressure of 196 kPa, and then hydrogen gas was blown into the autoclave over 3 hours at 80° C. under a hydrogen pressure of 196 kPa until the absorption of hydrogen gas in a volume of 400 mL was completed. After the replacement with nitrogen, the catalyst was filtered out and the resulting filtrate was concentrated under a reduced pressure of 1.33 kPa until the quantity thereof was reduced to 1.70 g. Further thereto, 50 mL of water and 10 g of a 25% aqueous solution of sodium hydroxide were added. The resulting solution was extracted with three 200 mL portions of ethyl acetate, and the organic layer was concentrated. The thus obtained solid was adsorbed to NH₂-modified silica gel (produced by Biotage Japan, Ltd.), and eluted with ethylacetate. The fraction obtained was concentrated, and the crystals thus deposited were dried to give 0.20 g of the entitled compound as light yellow crystals. Yield rate: 20%, EI-MS: (m/z) 188 (M⁺), melting point: 102-104° C.

Example 4

Synthesis of 1-Benzyl-4-(5'-methyl-2'-pyridyl)-1,2,5,6-tetrahydropyridine ((I)-14)

Benzyl bromide in an amount of 1.06 g was added to a solution of 1 g of 5-methyl-2,4'-bipyridine in 15 mL of isopropyl alcohol, and stirred for 5 hours at 50° C. To the resulting reaction solution, 0.08 g of 2% platinum carbon and 0.59 g of triethylamine were added. This admixture was put in an autoclave, the autoclave's atmosphere was replaced twice with nitrogen gas under a nitrogen pressure of 196 kPa, and then hydrogen gas was blown into the autoclave over 3 hours at 55° C. under a hydrogen pressure of 390 kPa until the absorption of hydrogen gas in a volume of 260 mL was completed. After the replacement with nitrogen, the catalyst was filtered out and the resulting filtrate was concentrated under a reduced pressure of 1.33 kPa until the quantity thereof was reduced to 1.70 g. Further thereto, 50 mL of water and 10 g of a 25% aqueous solution of sodium hydroxide were added. The resulting solution was extracted with three 50 mL portions of ethyl acetate. The organic layer was concentrated, and the thus obtained solid was adsorbed to 40 μm silica gel (produced by J.T. Baker, Inc.), and eluted with ethyl acetate. The fraction obtained was concentrated, and the crystals thus deposited were dried to give 0.50 g of the intended compound as light yellow crystals. Yield rate: 32%, EI-MS: (m/z) 264 (M⁺), melting point: 71.4-73.4° C.

The following compounds were synthesized in the similar manner to the above. The structural formulae of the compounds synthesized are illustrated below, and their physical properties are shown in Tables 1 to 6. As to the compounds whose melting points were impossible to measure and some others, their NMR spectral data are shown in the tables.

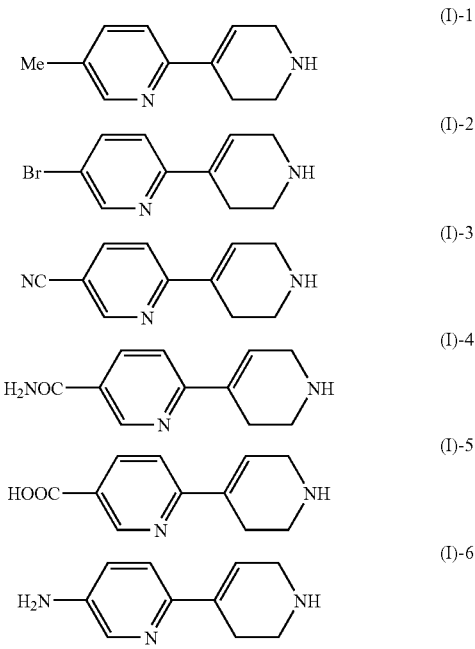

-continued
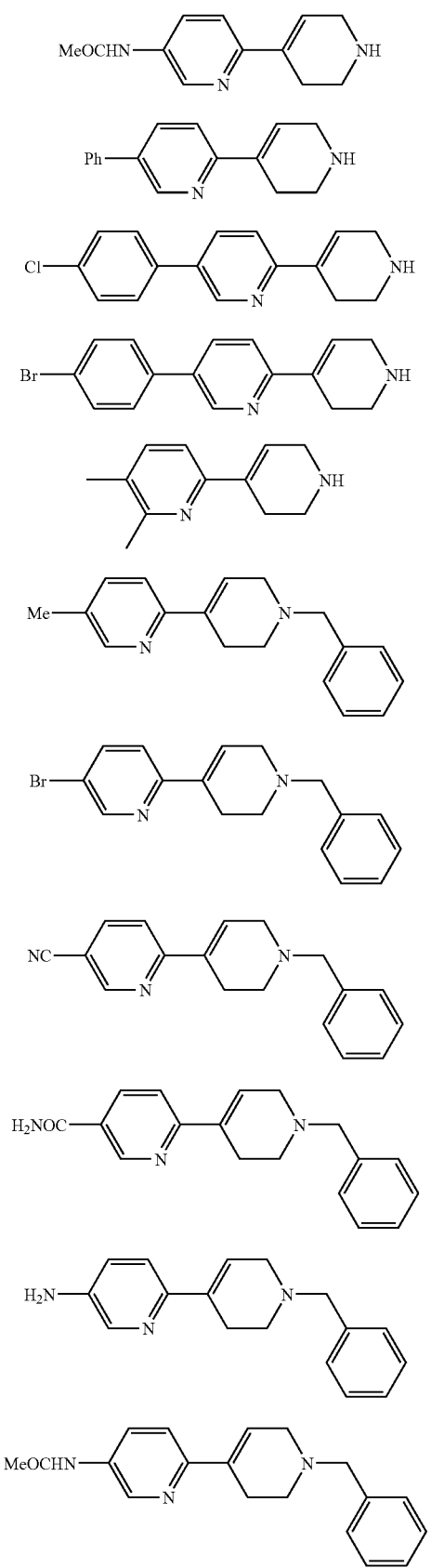
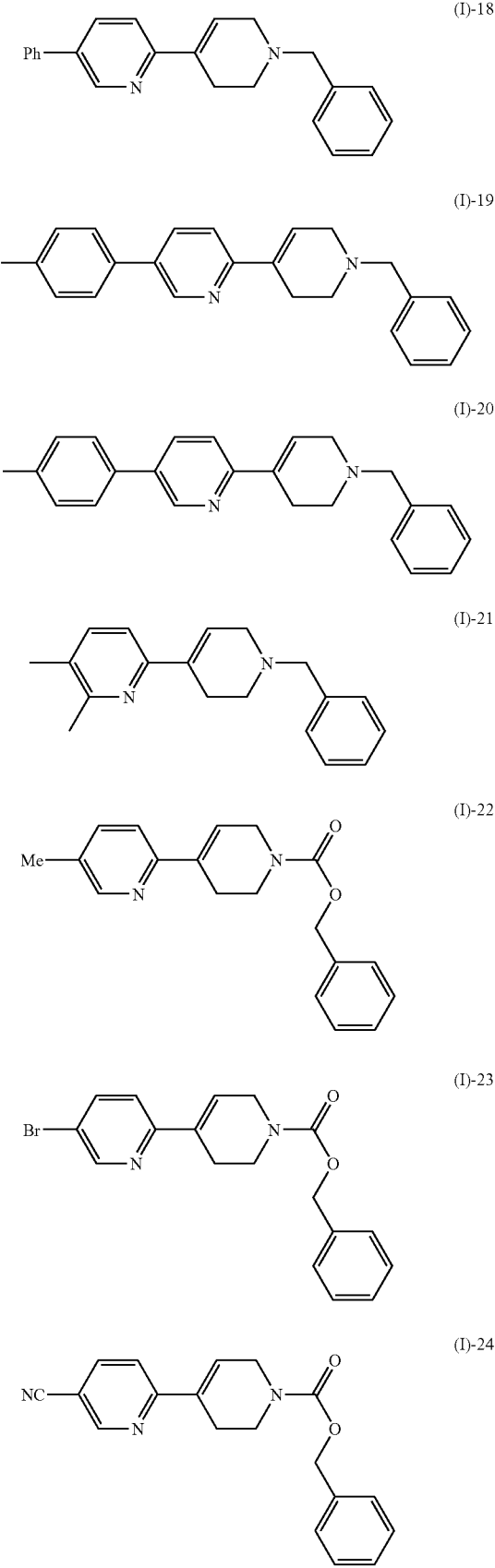

-continued
(I)-25 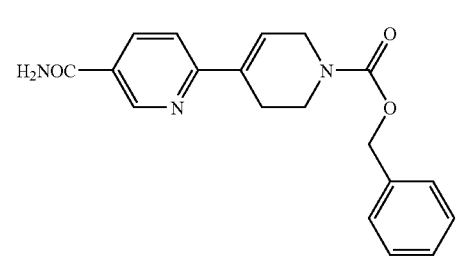
(I)-26 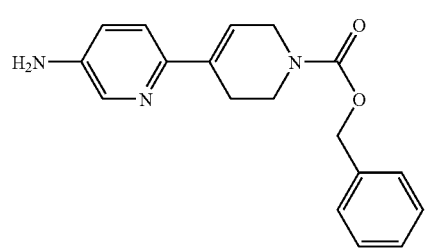
(I)-27 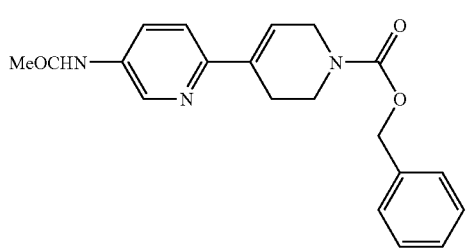
(I)-28 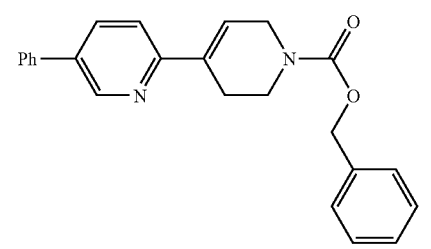
(I)-29 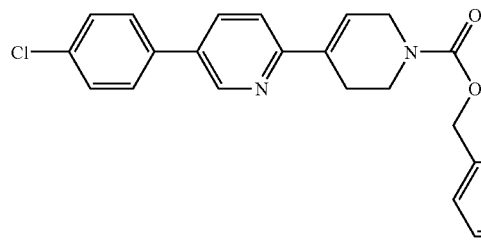
(I)-30 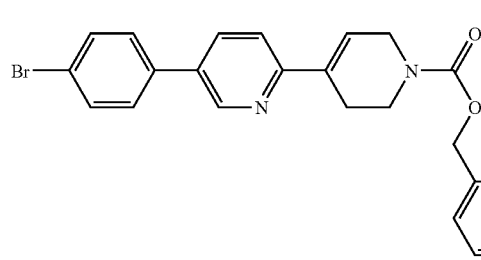
-continued
(I)-31 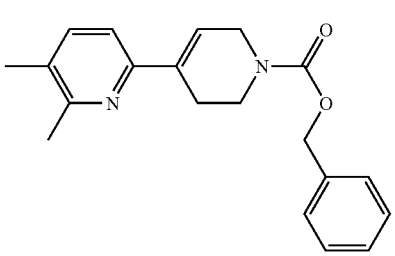
(I)32 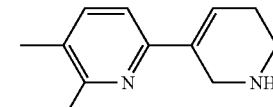
(I)-33 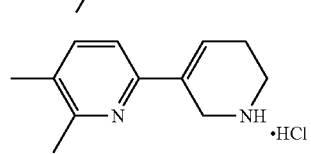
(I)-34 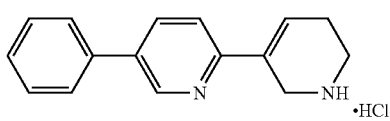
(II)-1 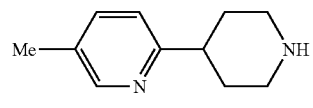
(II)-2 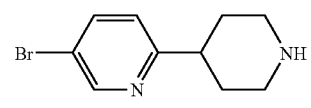
(II)-3 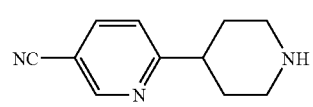
(II)-4 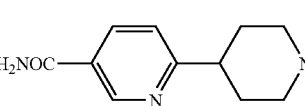
(II)-5 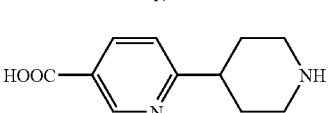
(II)-6 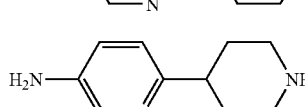
(II)-7 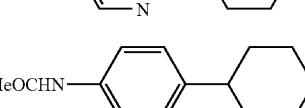
(II)-8 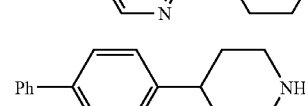
(II)-9 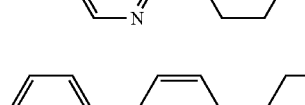

-continued
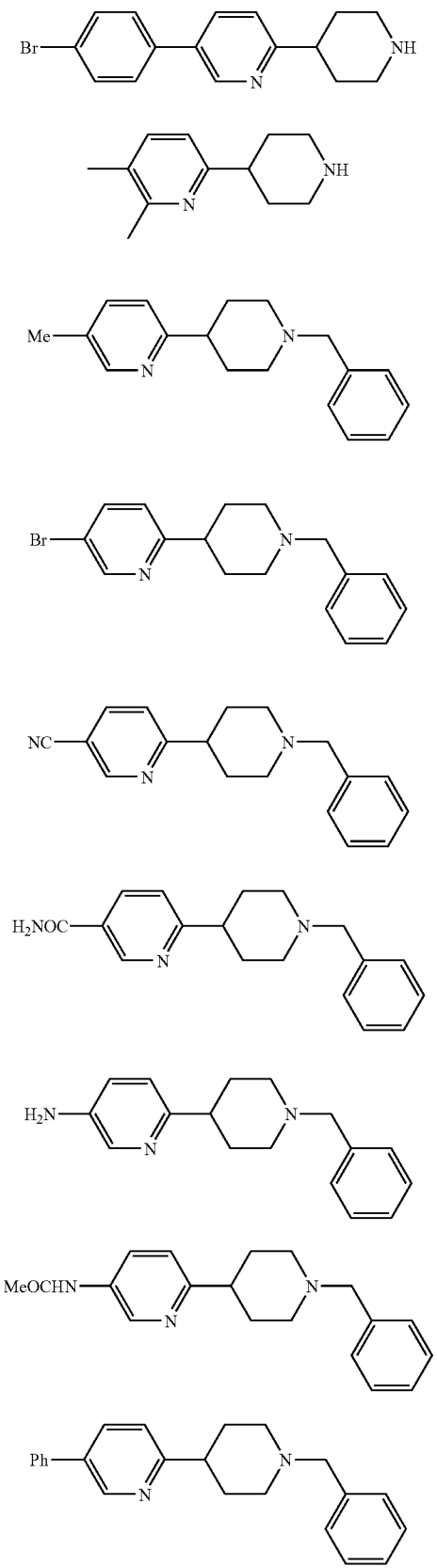
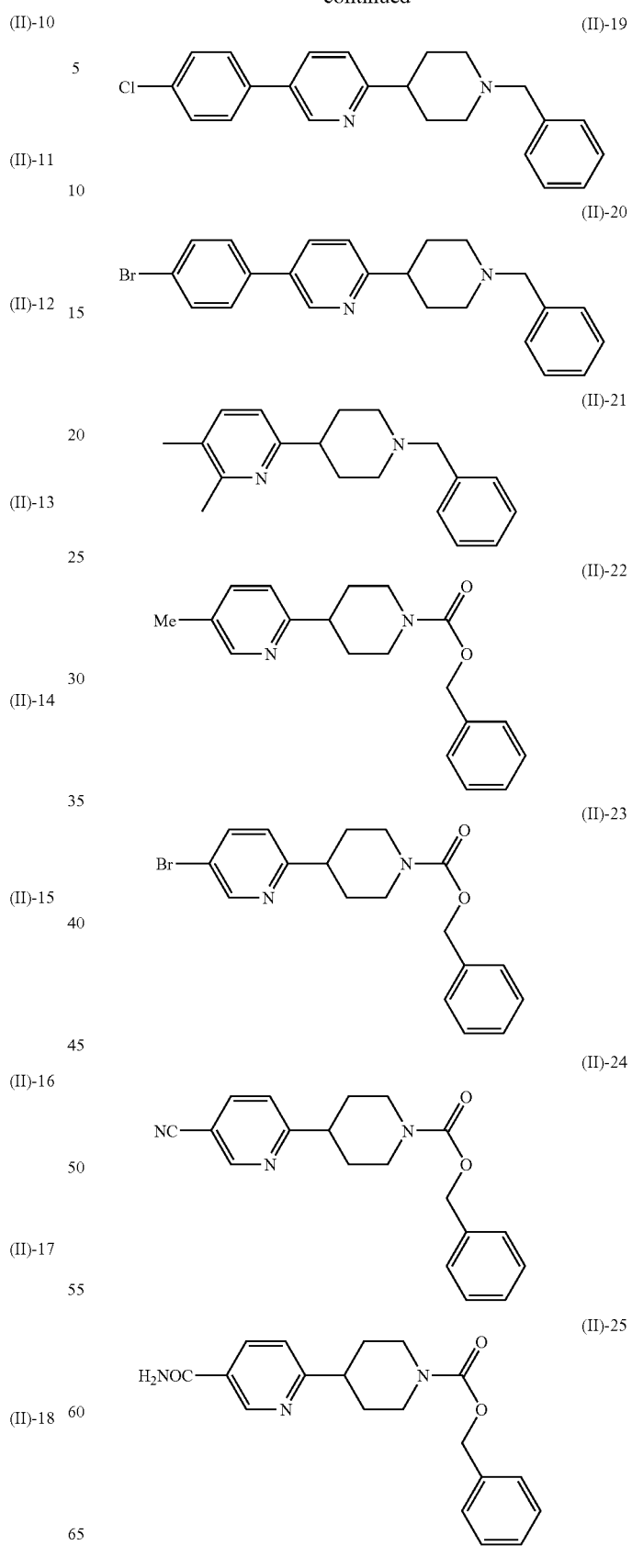

-continued

-continued

-continued
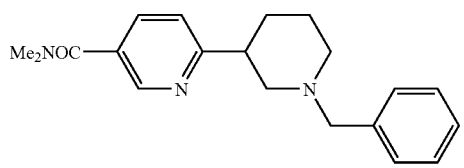
(IV)-8
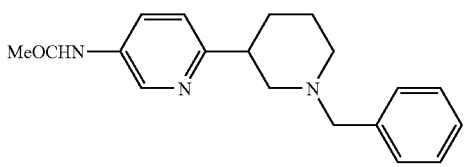
(IV)-9
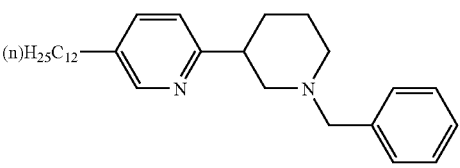
(IV)-10
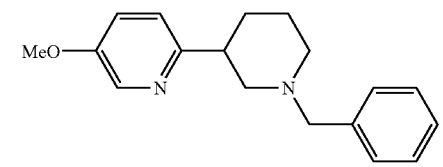
(IV)-11
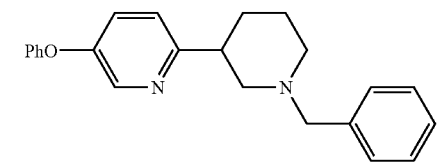
(IV)-12
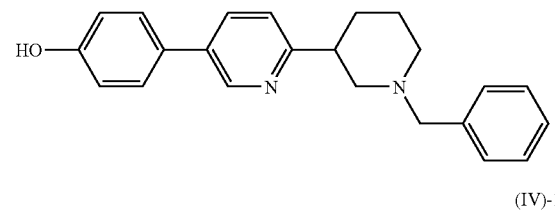
(IV)-13
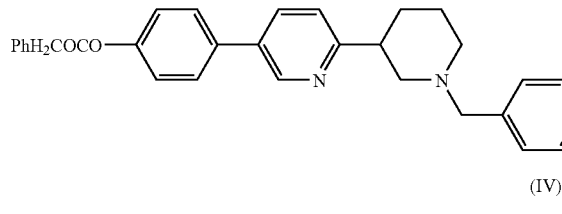
(IV)-14
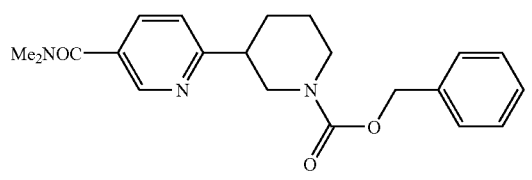
(IV)-15
-continued
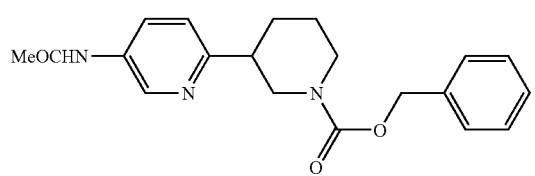
(IV)-16
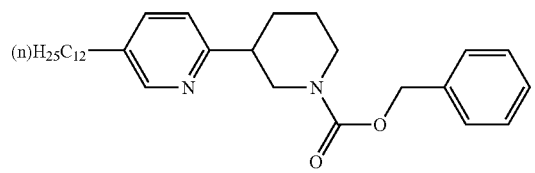
(IV)-17
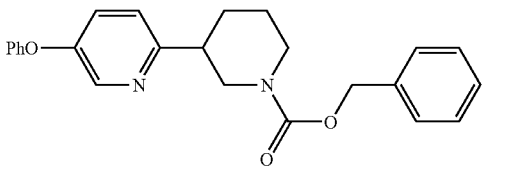
(IV)-18
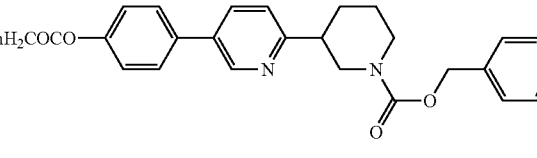
(IV)-19
TABLE 1
| Example | Compound Number | Melting Point (° C.) | MS [EI M+] |
|---|---|---|---|
| 5 | (I)-1 | 78.0-80.0 | 174 |
| 6 | (I)-2 | 73.0-74.0 | 239 |
| 7 | (I)-3 | 75.0-77.0 | 185 |
| 8 | (I)-4 | 163.0-165.0 | 203 |
| 9 | (I)-5 | 94.0-96.9 | 204 |
| 10 | (I)-6 | 90.0-92.3 | 175 |
| 11 | (I)-7 | 140.0-142.0 | 217 |
| 12 | (I)-8 | 148.0-150.9 | 236 |
| 13 | (I)-9 | 134.0-136.7 | 270 |
| 14 | (I)-10 | 131.0-132.2 | 315 |
| 15 | (I)-11 | 81.0-83.0 | 188 |
| 16 | (I)-12 | 71.4-73.4 | 264 |
| 17 | (I)-13 | 79.0-81.0 | 328 |
| 18 | (I)-14 | 78.0-107.0 | 275 |
| 19 | (I)-15 | 178.0-180.0 | 293 |
| 20 | (I)-16 | 113.0-115.4 | 265 |
| 21 | (I)-17 | 178.0-180.0 | 307 |
| 22 | (I)-18 | 149.0-150.9 | 326 |
| 23 | (I)-19 | 128.0-130.0 | 360 |
| 24 | (I)-20 | 138.0-140.0 | 405 |
| 25 | (I)-21 | 68.0-70.0 | 278 |
| 26 | (I)-22 | 60.0-63.0 | 308 |
| 27 | (I)-23 | 98.0-99.1 | 372 |
| 28 | (I)-24 | 95.0-97.0 | 319 |
| 29 | (I)-25 | 168.0-170.0 | 337 |
| 30 | (I)-26 | 88.0-90.5 | 309 |
| 31 | (I)-27 | 157.0-158.9 | 351 |
| 32 | (I)-28 | 125.0-126.9 | 370 |
| 33 | (I)-29 | 109.0-110.9 | 404 |
| 34 | (I)-30 | 145.0-147.3 | 449 |
| 35 | (I)-31 | 63.0-65.0 | 322 |
| 36 | (I)-32 | 102.0-104.0 | 188 |

TABLE 1-continued

| Example | Compound Number | Melting Point (° C.) | MS [EI M+] |
|---|---|---|---|
| 37 | (I)-33 | 158-181 | 188 |
| 38 | (I)-34 | 232 decomp. | 236 |
| 39 | (II)-1 | 90.0-92.0 | 176 |
| 40 | (II)-2 | 79.0-81.7 | 241 |
| 41 | (II)-3 | 90.0-92.3 | 187 |
| 42 | (II)-4 | 178.0-180.1 | 205 |

TABLE 2

| Example | Compound number | Melting Point (° C.) | MS [EI M+] |
|---|---|---|---|
| 43 | (II)-5 | 92.0-94.1 | 206 |
| 44 | (II)-6 | <25 | 177 |
| 45 | (II)-7 | 40.0-42.0 | 219 |
| 46 | (II)-8 | 109.0-110.9 | 238 |
| 47 | (II)-9 | 130.0-132.2 | 272 |
| 48 | (II)-10 | 148.0-150.9 | 317 |
| 49 | (II)-11 | 95.0-97.6 | 190 |
| 50 | (II)-12 | 74.0-76.3 | 266 |
| 51 | (II)-13 | 94.0-96.7 | 331 |
| 52 | (II)-14 | 103.0-105.6 | 277 |
| 53 | (II)-15 | 173.0-175.0 | 295 |
| 54 | (II)-16 | <25 | 267 |
| 55 | (II)-17 | 148.0-149.1 | 309 |
| 56 | (II)-18 | 123.0-125.1 | 328 |
| 57 | (II)-19 | 132.0-134.9 | 362 |
| 58 | (II)-20 | 163.0-165.1 | 407 |
| 59 | (II)-21 | 63.0-65.0 | 280 |
| 60 | (II)-22 | 69.0-71.9 | 310 |
| 61 | (II)-23 | 92.0-94.1 | 374 |
| 62 | (II)-24 | 56.0-58.6 | 321 |
| 63 | (II)-25 | 153.0-155.0 | 339 |
| 64 | (II)-26 | 79.0-81.7 | 311 |
| 65 | (II)-27 | 115.0-117.2 | 353 |
| 66 | (II)-28 | 106.0-108.3 | 372 |
| 67 | (II)-29 | 115.0-117.2 | 406 |
| 68 | (II)-30 | 132.0-134.9 | 451 |
| 69 | (II)-31 | 65.0-67.5 | 324 |
| 70 | (II)-32 | 181-194 | 190 |
| 71 | (II)-33 | 228 decomp. | 238 |

TABLE 3

| Compound Number | Melting Point (° C.) | MS | $^1$H-NMR |
|---|---|---|---|
| (II)-6 | <25 | 177 | (CD$_3$OD)1.93-1.99(m, 2H), 2.05(d, J=12.8Hz, 2H), 2.86-2.93(m, 1H), 3.12(td, J=12.8Hz, 3.2Hz, 2H), 3.49(d, J=12.8Hz, 2H), 7.06-7.11(m, 2H), 7.95(s, 1H). |
| (II)-16 | <25 | 267 | (CDCl$_3$)1.73-1.88(m, 4H), 2.08(d, J=11.4Hz, 2H), 2.60(m, 1H), 3.00(d, J=11.4Hz, 2H), 3.53(s, 2H), 6.88-6.97(m, 2H), 7.22-7.35(m, 5H), 8.02(dd, J=8.4, 2.5Hz, 1H). |

TABLE 4

| Compound Number | Melting Point (° C.) | MS | $^1$H-NMR |
|---|---|---|---|
| (III)-1 | 73-75 | 239 | |
| (III)-2 | 106.5-109 | 205 | |
| (III)-3 | 173-174 | 175 | |
| (III)-4 | 162-163 | 328 | |
| (III)-5 | 260 dec. | 204 | |
| (III)-6 | 224-225 | 190 | |
| (III)-7 | 168-169 | 252 | |
| (III)-8 | <25 | 329 | (CDCl$_3$)2.37(m, 2H), 2.60(t, J=5.6Hz, 2H), 3.50(dd, J=2.4, 4.4Hz, 2H), 3.71(s, 2H), 6.64(m, 1H), 7.25(t, J=7.2Hz, 2H), 7.32(t, J=7.2Hz, 2H), 7.38(t, J=7.2Hz, 2H), 7.69(dd, J=2.4, 8.4Hz, 1H), 8.55(d, J=2.4Hz, 1H). |
| (III)-9 | 89-90 | 321 | |
| (III)-10 | <25 | 322 | (CDCl$_3$)1.43(t, J=7.2Hz, 3H), 2.43(m, 2H), 2.64(m, 2H), 3.58(s, 2H), 3.75(m, 2H), 4.38(q, J=7.2Hz, 2H), 6.84(m, 1H), 7.26-7.56(m, 6H), 8.21(m, 1H), 9.13(s, 1H). |
| (III)-11 | 99.3-101.1 | 295 | |
| (III)-12 | 158-159 | 307 | |
| (III)-13 | <25 | 418 | (CDCl$_3$)0.89(t, J=6.7Hz, 3H), 1.27-1.31(m, 17H), 1.60(m, 2H), 1.71(m, 1H), 2.39(m, 2H), 2.56-2.63(m, 4H), 3.57(s, 2H), 3.74(s, 2H), 6.36(s, 1H), 6.60(m, 1H), 7.25-7.43(m, 7H). |
| (III)-14 | <25 | 280 | (CDCl$_3$)2.38(m, 2H), 2.65(t, J=5.7Hz, 2H), 3.55(m, 2H), 3.74(m, 2H), 3.86(s, 3H), 6.52(m, 1H), 7.14(m, 1H), 7.25-7.43(m, 6H), 8.24(d, J=2.9Hz, 1H). |
| (III)-15 | <25 | 342 | (CDCl$_3$)2.40(m, 2H), 2.63(t, J=5.8Hz, 2H), 3.56(m, 2H), 3.75(s, 2H), 6.58(m, 1H), 7.02(m, 2H), 7.15(t, J=7.3Hz, 1H), 7.24-7.43(m, 9H), 8.33(d, J=2.8Hz, 1H). |
| (III)-16 | <25 | 373 | (CDCl$_3$)2.37(brs, 2H), 3.64(t, J=5.6Hz, 2H), 4.47(dd, J=2.4, 4.8Hz, 2H), 5.19(s, 2H), 6.72(brs, 1H), 7.32(m, 6H), 7.75(dd, J=2.4, 8.4Hz, 1H), 8.58(d, J=2.0Hz, 1H). |
| (III)-17 | <25 | 366 | (CDCl$_3$)1.43(t, J=7.2Hz, 3H), 2.44(m, 2H), 3.68(t, J=5.7Hz, 2H), 3.96(s, 2H), 4.42(q, J=7.2Hz, 2H), 5.22(s, 2H), 6.92(m, 1H), 7.32-7.48(m, 6H), 8.25(dd, J=1.6, 8.4Hz, 1H), 9.16(s, 1H). |
| (III)-18 | 91-93 | 339 | |
| (III)-19 | 122-123 | 351 | |
| (III)-20 | 35-37 | 462 | |
| (III)-21 | <25 | 324 | (CDCl$_3$)2.38 (m, 2H), 3.67(t, J=5.7Hz, 2H), 3.88(s, 3H), 4.50(s, 2H), 5.22(s, 2H), 6.61(m, 1H), 7.18(m, 1H), 7.32-7.43(m, 6H), 8.28(s, 1H). |
| (III)-22 | <25 | 386 | (CDCl$_3$)2.44(m, 2H), 2.68(t, J=5.7Hz, 2H), 4.51(s, 2H), 5.21(s, 2H), 7.05(d, J=8.0Hz, 2H), 7.21(m, 1H), 7.32-7.43(m, 10H), 8.38(s, 1H) |

TABLE 4-continued

| Compound Number | Melting Point (° C.) | MS | ¹H-NMR |
|---|---|---|---|
| (III)-23 | <25 | 238 | (DMSO)2.47(m, 2H), 2.99(s, 3H), 3.30(t, J=5.6Hz, 2H), 4.23(M, 2H), 6.95(m, 1H), 7.57(t, J=6.2Hz, 1H), 7.87(d, J=8.1Hz, 1H), 8.12(t, J=7.2Hz, 1H), 8.63(d, J=5.0Hz, 1H). |

TABLE 5

| Compound Number | Melting Point (° C.) | MS | ¹H-NMR |
|---|---|---|---|
| (IV)-1 | <25 | 233 | (DMSO)1.70(m, 1H), 1.84(m, 2H), 2.02(m, 1H), 2.89(m, 1H), 2.92(s, 3H), 2.99(s, 3H), 3.18(m, 1H), 3.27(m, 2H), 3.43(m, 1H), 7.53(d, J=8.4Hz, 1H), 8.26(dd, J=8.4, 2.4Hz, 1H), 9.00(s, 1H). |
| (IV)-2 | 147-148 | 177 | (CDCl₃)1.79-1.89(m, 3H), 1.98(d, J=6.0Hz, 1H), 2.83(m, 1H), 3.25(d, J=10.8Hz, 2H), 3.42(m, 2H), 7.63(s, 2H), 7.95(s, 1H), 9.37(m, 1H), 9.61(m, 1H) |
| (IV)-3 | 50-51 | 330 | (DMSO)0.83(t, J=6.6Hz, 3H), 1.22(m, 13H), 1.27(m, 5H), 1.59(m, 2H), 1.89(m, 3H), 2.04(m, 1H), 2.74(t, J=7.8Hz, 2H), 2.86(m, 1H), 3.27(d, J=12.0Hz, 1H), 3.42(m, 1H), 3.48(d, J=12.0Hz, 1H), 3.62(m, 1H), 7.93(d, J=7.8Hz, 1H), 8.40(d, J=7.8Hz, 1H), 8.70(s, 1H), 9.52(m, 1H), 9.87(m, 1H). |
| (IV)-4 | <25 | 254 | (CDCl₃)1.65-1.90(m, 3H), 2.06(m, 1H), 2.89(d, J=12.0Hz, 1H), 3.29(q, J=11.4Hz, 1H), 3.48(d, J=12.0Hz, 1H), 3.57(m, 1H), 6.94(d, J=8.4Hz, 2H), 7.68(d, J=8.4Hz, 1H), 7.86(d, J=8.4Hz, 1H), 8.55(d, J=7.2Hz, 1H), 8.93(d, 1H), 9.48(m, 1H), 9.69(m, 1H) |
| (IV)-5 | 88-89 | 192 | |
| (IV)-6 | 179-180 | 254 | (DMSO)1.68-1.72(m, 1H), 1.84(m, 2H), 2.00(m, 1H), 2.86(m, 1H), 3.15(m, 1H), 3.27(m, 2H), 3.40(d, J=11.4Hz, 1H), 7.07(d, J=7.8Hz, 2H), 7.20(t, J=7.8Hz, 1H), 7.43(t, J=7.8Hz, 2H), 7.48(d, J=8.4Hz, 1H), 7.54(m, 1H), 8.36(s, 1H), 7.26(m, 1H), 7.30(m, 1H) |
| (VI)-7 | <25 | 206 | (DMSO)1.70(m, 1H), 1.84(m, 2H), 2.02(m, 1H), 2.89(m, 1H), 3.18(m, 1H), 3.27(m, 2H), 3.43(m, 1H), 7.49(d, J=7.8Hz, 1H), 7.90(dd, J=8.4, 2.4Hz, 1H), 8.59(s, 1H). |
| (VI)-8 | <25 | 323 | (CDCl₃)1.58-1.65(m, 1H), 1.79(m, 2H), 1.97(m, 1H), 2.13(m, 1H), 2.34(m, 1H), 2.95-3.09(m, 4H), 3.01(s, 3H), 3.11(s, 3H), 3.62(s, 3H), 7.23(d, J=7.8Hz, 1H), 7.25(m, 1H), 7.32(t, J=7.5Hz, 1H), 7.36(d, J=7.2Hz, 2H), 7.67(dd, J=2.4, 7.8Hz, 1H), 8.58(m, 1H). |

TABLE 5-continued

| Compound Number | Melting Point (° C.) | MS | ¹H-NMR |
|---|---|---|---|
| (IV)-9 | <25 | 309 | (D₂O)1.57(dq, J=3.0, 12.0Hz, 1H), 1.80(d, J=7.8Hz, 1H), 1.90(m, 1H), 1.95(d, J=11.4Hz, 1H), 2.21(s, 3H), 2.24(m, 1H), 2.45(m, 1H), 3.04(m, 1H), 3.15(m, 2H), 3.73(m, 2H), 7.09(d, J=8.4Hz, 1H), 7.29(d, J=7.2Hz, 1H), 7.34(t, J=7.2Hz, 2H), 7.42(d, J=12.6Hz, 2H), 8.01(d, J=6.6Hz, 1H), 8.53(s, 1H). |
| (IV)-10 | <25 | 420 | (CDCl₃)0.88(t, J=7.2Hz, 3H), 1.25(m, 13H), 1.29(m, 5H), 1.55-1.63(m, 3H), 1.78(m, 2H), 1.96(m, 1H), 2.08(m, 1H), 2.27(m, 1H), 2.54(t, J=7.8Hz, 2H), 2.94(m, 1H), 3.03(m, 1H), 3.08(m, 1H), 3.60(s, 2H), 7.08(d, J=8.4Hz, 1H), 7.24(dd, J=7.2Hz, 1H), 7.30(t, J=7.2Hz, 2H), 7.35(d, J=7.2Hz, 2H), 7.39(dd, J=2.4, 8.4Hz, 1H), 8.34(s, 1H). |

TABLE 6

| Compound Number | Melting Point (° C.) | MS | ¹H-NMR |
|---|---|---|---|
| (IV)-11 | <25 | 282 | (DMSO)1.58(m, 1H), 1.74-1.77(m, 2H), 1.94(m, 1H), 2.05(m, 2H), 2.91-3.06(m, 4H), 3.57(s, 2H), 3.81(s, 3H), 7.08-7.12(m, 2H), 7.24(t, J=7.2Hz, 1H), 7.30(t, J=7.2Hz, 2H), 7.35(m, 2H), 8.22(d, J=3.0Hz, 1H). |
| (IV)-12 | <25 | 344 | (D₂O)1.60(m, 1H), 1.81(m, 1H), 1.93-2.00(m, 2H), 2.20(m, 1H), 2.43(m, 1H), 3.04(m, 1H), 3.18(m, 2H), 3.73(m, 2H), 6.99(d, J=8.4, 2H), 7.12-7.15(m, 2H), 7.20(dd, J=3, 9Hz, 1H), 7.28(m, 1H), 7.32-7.36(m, 4H), 7.41(m, 2H), 8.31(s, 1H). |
| (IV)-13 | <25 | 344 | (CDCl₃)1.61-1.71(m, 1H), 1.88(m, 1H), 2.05(m, 1H), 2.17(m, 1H), 2.42(m, 1H), 2.78(m, 1H), 3.23-3.49(m, 3H), 3.90-4.01(m, 2H), 6.97(d, J=12.6Hz, 2H), 7.12(d, J=12.6Hz, 1H), 7.30-7.41(m, 6H), 7.5-7.52(m, 2H), 7.63(d, J=12.6Hz, 1H), 8.61(s, 1H) |
| (IV)-14 | <25 | 462 | (CDCl₃)1.65-1.70(m, 1H), 1.83(m, 1H), 1.92(m, 1H), 2.01(m, 1H), 2.22(m, 1H), 2.50(m, 1H), 3.06(m, 1H), 3.21(m, 2H), 3.80(m, 2H), 5.29(m, 2H), 7.25-7.30(m, 4H), 7.34(t, J=7.8Hz, 2H), 7.37-7.43(m, 5H), 7.46(m, 2H), 7.54(d, J=7.2Hz, 2H), 7.78(d, J=7.2Hz, 1H), 8.71(s, 1H). |
| (IV)-15 | <25 | 367 | (CDCl₃)1.63(m, 1H), 1.80(m, 2H), 2.04(m, 2H), 2.91(m, 3H), 3.02(s, 3H), 3.13(m, 4H), 4.21(m, 1H), 4.31(m, 1H), 5.16(m, 2H), 7.23(m, 1H), 7.36(m, 5H), 7.72(m, 1H), 8.61(s, 1H). |

TABLE 6-continued

| Compound Number | Melting Point (° C.) | MS | $^1$H-NMR |
|---|---|---|---|
| (IV)-16 | <25 | 353 | (CDCl$_3$)1.48(m, 1H), 1.68-1.73(m, 2H), 1.94(d, J=11.4Hz, 1H), 2.05(s, 3H), 2.74(m, 1H), 2.76-2.90(m, 2H), 4.03(d, J=13.8Hz, 1H), 4.13(m, 1H), 5.09(m, 2H), 7.24-7.36(m, 6H), 7.96(m, 1H), 8.58 (s, 1H), 10.10(s, 1H). |
| (IV)-17 | <25 | 464 | (DMSO)0.88(t, J=7.2Hz, 3H), 1.28-1.30(m, 20H), 1.59(m, 2H), 1.78(m, 2H), 2.04(m, 1H), 2.57(t, J=7.8Hz, 2H), 2.84(m, 2H), 3.08(m, 1H), 5.16(m, 2H), 7.09(m, 1H), 3.62(m, 1H), 7.30-7.36(m, 5H), 7.43(m, 1H), 8.36(s, 1H). |
| (IV)-18 | <25 | 388 | (D$_2$O)1.62(m, 1H), 1.79(m, 2H), 2.06(m, 1H), 2.91(m, 2H), 3.11(m, 1H), 4.17-4.33(m, 2H), 5.09-5.30(m, 2H), 7.01(d, J=8.4Hz, 2H), 7.16(t, J=8.4Hz, 2H), 7.31-7.40(m, 8H), 8.33(s, 1H). |
| (IV)-19 | <25 | 506 | (CDCl$_3$)1.64(m, 1H), 1.72(m, 2H), 2.10(m, 1H), 2.94(m, 2H), 3.16(m, 1H), 4.33(m, 2H), 5.17(m, 2H), 5.30(s, 2H), 7.29-7.47(m, 13H), 7.56(d, J=11.5Hz, 2H), 7.80(s, 1H), 8.74(s, 1H). |

Comparative Example 1

Synthesis of 4-(5'-Methylpyrid-2'-yl)piperidine

To a solution of 10 g of 5-methyl-2,4'-bipyridine in 70 ml of isopropyl alcohol, 10.5 g of benzyl bromide was added, and stirred for 5 hours at 50° C. The resulting reaction solution was cooled, and thereby crystals separated out. These crystals were filtered off, and dried. Thus, 18.4 g of light brown crystals were obtained, and dissolved in 200 mL of ethanol. The resulting solution was cooled to 10° C., and thereto 4.9 g of sodium tetrahydroborate was added. The resulting reaction solution was refluxed for 3 hours, concentrated to dryness, passed through a silica gel column (40 µm, made by J.T. Baker, Inc.) and then eluted with ethyl acetate. Further, the fraction thus obtained was concentrated to give 11.3 g of light brown crystals. The crystals thus obtained were dissolved in 300 mL of toluene, and dehydrated over 3 hours under reflux by use of a Dean-Stark reflux dehydrator. The reaction solution was cooled to room temperature, and thereto 7.7 g of Z-Chloride (produced by Wako Pure Chemical Industries, Ltd.) was added. The reaction solution was refluxed for 5 hours, concentrated to dryness, passed through a silica gel column (40 µm, made by J.T. Baker, Inc.), and then eluted with toluene. Further, the fraction thus obtained was concentrated to give 6.6 g of light brown crystals. The crystals thus obtained were dissolved in 19 mL of hydrochloric acid, and the reaction solution was refluxed for 3 hours. The resulting reaction solution was cooled to room temperature, adjusted to pH 13 by addition of sodium hydroxide, and then extracted with chloroform. Together with the organic layer, the extract was dried over anhydrous magnesium sulfate, and the inorganic matter was filtrated out. The resulting organic layer was concentrated, and the crystals thus deposited were dried to give 2.6 g of light yellow oily matter. Then, the oily matter was dissolved in 70 mL of methanol, and thereto 1.35 g of 10% palladium carbon and 2.96 g of ammonium formate were added. This admixture was put in an autoclave, the autoclave's atmosphere was replaced twice with nitrogen gas under a nitrogen pressure of 196 kPa, and then hydrogen gas was blown into the autoclave over 5 hours at 80° C. under a hydrogen pressure of 490 kPa until the absorption of hydrogen gas in a volume of 340 mL was completed. After the replacement with nitrogen, the catalyst was filtered out and the resulting filtrate was concentrated under a reduced pressure of 1.33 kPa until the quantity thereof was reduced to 10.0 g. Further thereto, 50 mL of water and 10 g of a 25% aqueous solution of sodium hydroxide were added. The resulting solution was extracted with three 200 mL portions of ethyl acetate, and the organic layers were mixed together and dried over anhydrous magnesium sulfate. Then, the inorganic matter was filtered out, and the organic layer thus obtained was concentrated. The thus deposited crystals were dried to give 1.9 g of the intended compound as light yellow oily matter.

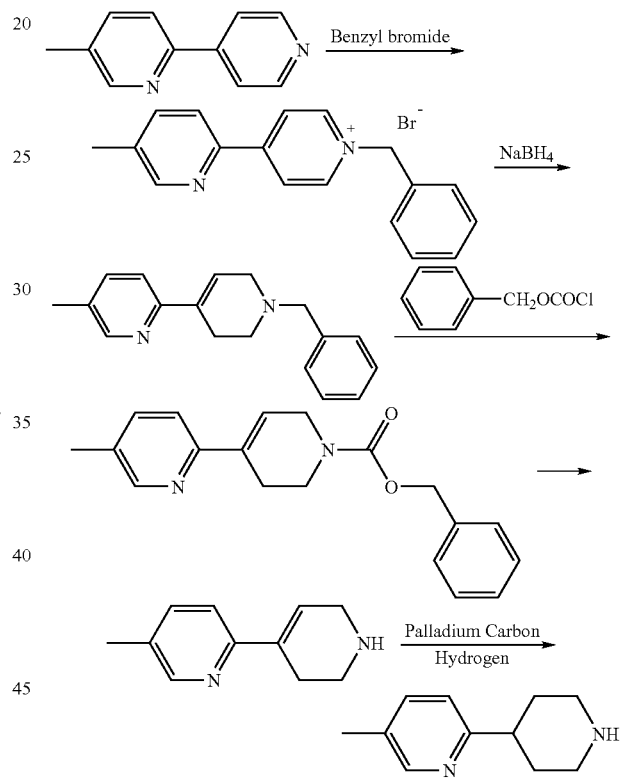

The results of Example 1 and Comparative Example 1 are shown in Table 7. The reaction time set forth in the table is the sum total of reaction times in all the steps.

TABLE 7

|  | Example 1 | Comparative Example 1 |
|---|---|---|
| Total Yield (%) | 48 | 20 |
| Number of Steps | 2 | 6 |
| Reaction Time (hr) | 10 | 24 |

As is evident from the results shown in Table 7, the synthesis according to the combination of known methods is three times greater in number of steps and 2.4 times longer in reaction time required than the present synthesis. In addition, the yield was 48% in Example 1, whereas Comparative Example 1 gave a low yield of 20%. From these data, it is apparent that the present manufacturing method is superior.

The invention claimed is:

1. A compound represented by the following formula (I) or a salt thereof;

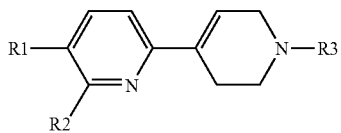

wherein
R1 represents an alkyl group, an alkenyl group, an alkynyl group, an aryl group, an alkoxy group, an aryloxy group, a formyl group, a carboxyl group, a carbonyl group, an oxycarbonyl group, a sulfonyl group, a carbamoyl group, a sulfamoyl group, a thiol group, an alkylthio group, an arylthio group, a thiocarbonyl group, a ureido group, an amino group, a carbonylamino group, a sulfonylamino group, a cyano group, a heterocycle residue, a fluorine atom, a bromine atom or an iodine atom,
R2 represents a hydrogen atom or an alkyl group, and
R3 represents a hydrogen atom, an alkyl group, a formyl group, a carboxyl group, a carbonyl group, an oxycarbonyl group, a sulfonyl group, a carbamoyl group or a sulfamoyl group.

2. The compound represented by formula (I) or a salt thereof according to claim 1, wherein R1 is selected from the group consisting of a 1-12C alkyl group, a 6-10C aryl group, a substituted or unsubstituted amino group, a bromine atom and an iodine atom.

* * * * *